(12) United States Patent
Brown

(10) Patent No.: US 9,204,730 B2
(45) Date of Patent: Dec. 8, 2015

(54) ARTICULATED HUMAN ARM SUPPORT

(76) Inventor: Garrett W. Brown, Philadelphia, PA (US)

(*) Notice: Subject to any disclaimer, the term of this patent is extended or adjusted under 35 U.S.C. 154(b) by 189 days.

(21) Appl. No.: 12/674,731

(22) PCT Filed: Aug. 28, 2008

(86) PCT No.: PCT/US2008/074554
§ 371 (c)(1),
(2), (4) Date: Feb. 23, 2010

(87) PCT Pub. No.: WO2009/029693
PCT Pub. Date: Mar. 5, 2009

(65) Prior Publication Data
US 2011/0127390 A1    Jun. 2, 2011

Related U.S. Application Data

(60) Provisional application No. 60/968,974, filed on Aug. 30, 2007.

(51) Int. Cl.
*A47C 7/54* (2006.01)
*B43L 15/00* (2006.01)
*F16M 11/04* (2006.01)
(Continued)

(52) U.S. Cl.
CPC ... *A47C 7/54* (2013.01); *A47C 1/03* (2013.01); *A47C 7/52* (2013.01); *A61B 19/26* (2013.01); *A61F 5/3761* (2013.01); *B43L 15/00* (2013.01); *F16M 11/04* (2013.01); *F16M 13/04* (2013.01);
(Continued)

(58) Field of Classification Search
CPC ............ A47C 1/03; A47C 7/54; B43L 15/00; F16M 11/04; F16M 13/04; A61B 2019/265; A61B 19/26

USPC ........................ 248/118, 118.1, 118.3, 118.5;
297/411.21, 411.22, 411.23, 411.32,
297/411.33, 411.34, 411.35, 411.37,
297/411.39, 411.2, 411.46, 423.39, 423.43,
297/411.25, 411.29, 411.31, 411.38,
297/411.36; 5/621, 623, 624, 646, 648
See application file for complete search history.

(56) References Cited

U.S. PATENT DOCUMENTS 1,070,525 A    8/1912    Pieper
1,494,638 A    5/1924    Sheldon
(Continued)

FOREIGN PATENT DOCUMENTS

AU    WO 03/046431 A1    6/2003
DE    8904387 U1    6/1989
(Continued)

OTHER PUBLICATIONS

Information Disclosure Statement dated Jan. 13, 2010 for U.S. Appl. No. 11/859,526.
(Continued)

*Primary Examiner* — Terrell McKinnon
*Assistant Examiner* — Eret McNichols
(74) *Attorney, Agent, or Firm* — Barnes & Thornburg LLP; Joan T. Kluger

(57) ABSTRACT

An upper body appendage support apparatus having an articulating parallelogram support structure connected to an articulating upper body appendage support structure, the latter accommodating a user's forearm, wrist, and/or heel-of-hand. The apparatus analogously jointed to the human arm and moving synchronously therewith.

29 Claims, 23 Drawing Sheets

(51) Int. Cl.
*F16M 13/04* (2006.01)
*A47C 1/03* (2006.01)
*A61F 5/37* (2006.01)
*A47C 7/52* (2006.01)
*A61B 19/00* (2006.01)
*A47B 21/03* (2006.01)

(52) U.S. Cl.
CPC ..... *A47B 21/0371* (2013.01); *A47B 2200/0092* (2013.01); *A61B 2019/265* (2013.01)

(56) References Cited

U.S. PATENT DOCUMENTS

| | | | |
|---|---|---|---|
| 1,505,567 A | | 8/1924 | Kelley |
| 1,639,815 A | * | 8/1927 | Siebrandt ........................ 602/16 |
| 1,674,669 A | | 6/1928 | Percy |
| 2,036,097 A | | 3/1936 | Pieper |
| 2,076,446 A | | 4/1937 | Carwardine |
| 2,090,439 A | | 8/1937 | Carwardine |
| 2,700,524 A | | 1/1955 | Lauterbach |
| 2,941,776 A | | 6/1960 | Lauterbach |
| 3,311,340 A | | 3/1967 | Riis |
| 3,333,613 A | | 8/1967 | Bosse |
| 3,393,938 A | * | 7/1968 | Meyer et al. .................. 297/397 |
| 3,409,261 A | | 11/1968 | Leporati |
| 3,426,190 A | | 2/1969 | Bobrick |
| 3,540,719 A | | 11/1970 | Romney |
| 3,694,888 A | | 10/1972 | Bosse |
| 3,917,200 A | | 11/1975 | Johnson |
| 4,080,530 A | | 3/1978 | Krogsrud |
| 4,156,512 A | | 5/1979 | Brown |
| 4,158,490 A | * | 6/1979 | Gottschalk et al. ........... 352/243 |
| 4,160,536 A | | 7/1979 | Krogsrud |
| 4,206,983 A | | 6/1980 | Nettman et al. |
| 4,208,028 A | * | 6/1980 | Brown et al. .................. 224/185 |
| 4,265,147 A | | 5/1981 | Fox |
| 4,394,075 A | | 7/1983 | Brown |
| 4,447,031 A | | 5/1984 | Souder et al. |
| 4,591,122 A | | 5/1986 | Kreuzer |
| RE32,213 E | | 7/1986 | Brown |
| 4,610,560 A | | 9/1986 | Miller |
| 4,669,451 A | * | 6/1987 | Blauth et al. .................... 601/33 |
| 4,700,827 A | | 10/1987 | Haaser |
| 4,744,019 A | | 5/1988 | Krogsrud |
| 4,796,162 A | | 1/1989 | Krogsrud |
| 4,805,615 A | | 2/1989 | Carol |
| 4,846,434 A | | 7/1989 | Krogsrud |
| 4,852,842 A | | 8/1989 | O'Neill |
| 4,953,822 A | | 9/1990 | Sharber et al. |
| 4,976,387 A | | 12/1990 | Spianti |
| 5,037,053 A | | 8/1991 | Fox et al. |
| 5,074,501 A | * | 12/1991 | Holtta ........................ 248/118.3 |
| 5,109,736 A | | 5/1992 | Dixon |
| 5,111,983 A | | 5/1992 | Simmons |
| 5,113,768 A | * | 5/1992 | Brown .......................... 104/112 |
| 5,135,190 A | | 8/1992 | Wilson |
| 5,340,072 A | | 8/1994 | Halbirt |
| 5,348,260 A | | 9/1994 | Acevedo |
| 5,360,196 A | | 11/1994 | DiGiulio et al. |
| 5,407,249 A | * | 4/1995 | Bonutti ..................... 297/411.35 |
| D358,832 S | | 5/1995 | Lenny et al. |
| 5,435,515 A | | 7/1995 | DiGiulio |
| 5,544,554 A | | 8/1996 | Brightly |
| 5,609,316 A | | 3/1997 | Tigliev |
| 5,669,122 A | | 9/1997 | Benoit |
| 5,713,591 A | * | 2/1998 | Zarkhin et al. ............. 280/250.1 |
| 5,797,054 A | * | 8/1998 | Paddock et al. ............... 396/421 |
| 5,857,815 A | | 1/1999 | Bailey et al. |
| 6,003,940 A | * | 12/1999 | Jackson ..................... 297/217.3 |
| 6,030,130 A | | 2/2000 | Paddock et al. |
| 6,042,064 A | | 3/2000 | Hong |
| 6,149,506 A | | 11/2000 | Duescher |
| 6,393,708 B1 | | 5/2002 | Culver et al. |
| 6,446,287 B2 | * | 9/2002 | Borders .......................... 5/618 |
| 6,464,183 B1 | * | 10/2002 | Bouhuijs ........................ 248/118 |
| 6,523,796 B2 | | 2/2003 | Abramowsky et al. |
| 6,592,085 B2 | * | 7/2003 | Iwata et al. ................. 248/118.1 |
| 6,708,935 B2 | | 3/2004 | Smeed |
| 6,711,972 B1 | | 3/2004 | Joyner et al. |
| 6,852,107 B2 | | 2/2005 | Wang et al. |
| 6,858,003 B2 | | 2/2005 | Evans |
| 6,896,230 B2 | | 5/2005 | Cvek |
| 6,923,505 B2 | | 8/2005 | Siminovitch et al. |
| 6,925,668 B2 | * | 8/2005 | Cuschieri et al. .................. 5/623 |
| 7,055,789 B2 | | 6/2006 | Libbey et al. |
| 7,290,744 B2 | | 11/2007 | Baldasari |
| 7,325,777 B2 | | 2/2008 | Thiessen |
| 7,412,754 B2 | | 8/2008 | Hanson |
| 7,618,016 B2 | * | 11/2009 | Brown .......................... 248/584 |
| 8,262,166 B2 | * | 9/2012 | Stuijt et al. ................ 297/411.35 |
| 2002/0134896 A1 | * | 9/2002 | Hunter .......................... 248/118 |
| 2004/0026584 A1 | | 2/2004 | Libbey et al. |
| 2004/0195883 A1 | | 10/2004 | Vrijlandt et al. |
| 2005/0012376 A1 | | 1/2005 | Siminovitch |
| 2005/0015879 A1 | | 1/2005 | Cuschieri |
| 2005/0023015 A1 | | 2/2005 | Argento |
| 2005/0023422 A1 | | 2/2005 | Oddsen |
| 2005/0043718 A1 | | 2/2005 | Madhani |
| 2005/0224670 A1 | | 10/2005 | Metelski |
| 2006/0186281 A1 | | 8/2006 | Thiessen |
| 2006/0231700 A1 | | 10/2006 | Orf et al. |
| 2007/0080275 A1 | | 4/2007 | Stachowski |
| 2007/0237572 A1 | | 10/2007 | Thiessen |
| 2008/0046122 A1 | | 2/2008 | Manzo |
| 2008/0106133 A1 | | 5/2008 | Vrijlandt et al. |
| 2008/0210842 A1 | | 9/2008 | Van Dorsser et al. |
| 2015/0129741 A1 | * | 5/2015 | Okuda .................. F16M 13/04 248/550 |
| 2015/0202017 A1 | * | 7/2015 | Nakamura ............. A61B 19/26 248/118 |

FOREIGN PATENT DOCUMENTS

| | | |
|---|---|---|
| EP | 0192253 | 8/1986 |
| EP | 0429008 | 5/1991 |
| EP | 1312251 | 5/2003 |
| EP | 1726412 A1 | 11/2006 |
| GB | 593231 | 10/1947 |
| GB | 2170651 | 8/1986 |
| GB | 2325393 | 11/1998 |
| JP | 2006101952 | 4/2006 |
| WO | 0016950 | 3/2000 |
| WO | 2006113416 | 10/2006 |
| WO | 20080112687 | 9/2008 |
| WO | 20060113416 | 10/2008 |

OTHER PUBLICATIONS

Office Action dated Oct. 13, 2006 for U.S. Appl. No. 11/060,612.
Response to Oct. 13, 2006 Office Action for U.S. Appl. No. 11/060,612.
Office Action dated Dec. 28, 2006 for U.S. Appl. No. 11/060,612.
Response to Dec. 28, 2006 Office Action for U.S. Appl. No. 11/060,612.
Office Action dated Jun. 19, 2007 for U.S. Appl. No. 11/060,612.
Response to Jun. 19, 2007 Office Action for U.S. Appl. No. 11/060,612.
Office Action dated Nov. 13, 2008 for U.S. Appl. No. 11/737,567.
Notice of Allowability dated Oct. 9, 2007 for U.S. Appl. No. 11/060,612.
Office Action dated Apr. 13, 2010 for U.S. Appl. No. 11/859,526.
Information Disclosure Statement dated Mar. 9, 2010 for U.S. Appl. No. 12/677,179.
International Search Report & Written Opinion dated Nov. 28, 2008 for PCT/US08/76331.
International Search Report & Written Opinion dated May 12, 2009 for PCT/US09/37384.
International Search Report and Written Opinion for PCT/US2008/074554.

(56) References Cited

OTHER PUBLICATIONS

Supplementary European Search Report dated Apr. 20, 2011 for European Patent Application No. 08799533.8.

Boudewijn M. Wisse, Wouter D. Van Dorsser, Rogier Barents, and Just L. Herfer, Energy-Free Adjustment of Gravity Equilibrators Using the Virtual Spring Concept, Proceedings of the 2007 IEEE 10th International Conference on Rehabilitation Robotics, Jun. 12-15, 2007, 742-750, Noordwijk, The Netherlands.

Just L. Herder, Development of a Statically Balanced Arm Support: ARMON, Proceedings of the 2005 IEEE 9th International Conference on Rehabilitation Robotics, Jun. 28-Jul. 1, 2005, 281286, Chicago, IL, USA.

Office Action dated Jan. 22, 2013 for Japan Patent Application No. 2010-523123.

Office Action dated Oct. 4, 2013 for JP Pat. App. No. 2010-523123.

First Notification of Examiner's Opinion issued on Aug. 31, 2011 for CN Pat. App. No. 200880105002.X.

Second Notification of Examiner's Opinion issued on Mar. 31, 2012 for CN Pat. App. No. 200880105002.X.

Extended European Search Report date Jul. 16, 2014 for European Patent Application No. 08828140.7.

\* cited by examiner

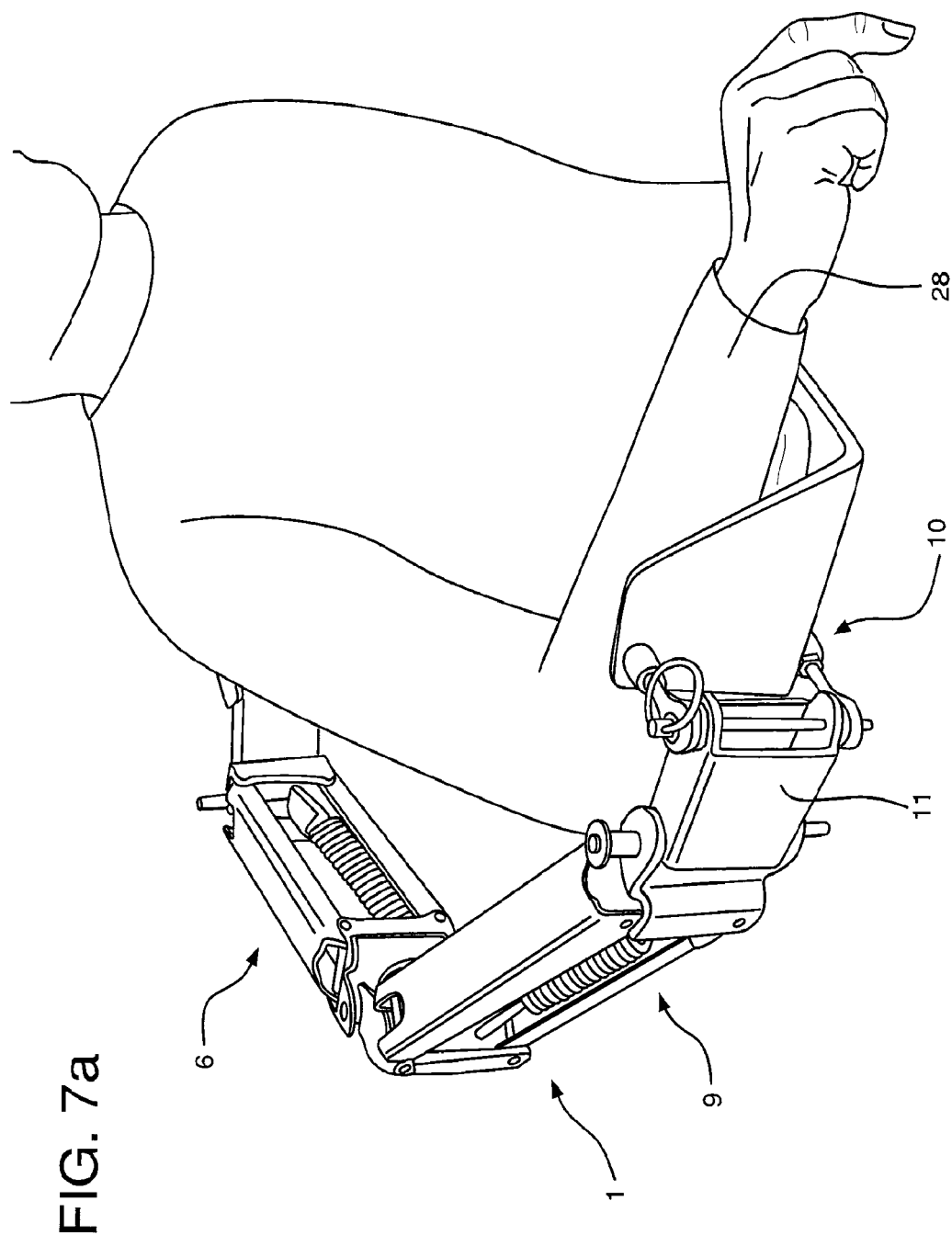

ARTICULATED HUMAN ARM SUPPORT

This application is based on, and claims priority to, U.S. provisional application No. 60/968,974, having a filing date of Aug. 30, 2007, and entitled Articulated Human Arm Support.

BACKGROUND OF THE INVENTION

Illustrative embodiments of the invention relate generally to ergonomic equipment for relieving repetitive workplace stresses, and more particularly to relieving cumulative stresses from work in which the unsupported, human arm, wrist and hand are engaged in protracted reaching.

Many scientific, medical and industrial tasks involve the hand deployment of lightweight objects or instruments, which must be held aloft and manipulated in space for extended periods of time. The act of 'pipetting,' (dispensing small amounts of liquid into numerous receptacles), for example, can require hours of delicate iterations during which the practitioner's arms remain essentially unsupported. The resulting repetitive stresses are known to be a cause of work-related shoulder and forearm trauma, including rotator cuff and carpal tunnel injuries. Fixed arm supports and supports that permit some lateral motion are known in the art and offer limited forearm and/or wrist relief. Problems arise, however, in connection with the high percentage of such tasks that protractedly require a larger—often much larger—range of horizontal and vertical motions.

Medical and scientific tasks may involve only lightweight hand-manipulated instruments and devices, but the stress on the practitioner can still be severe, due merely to the outstretched, unsupported weight of his or her arm(s) for the extended duration of these operations. Known 'ergonomic' shelf supports, including those on swing arms that provide a degree of lateral freedom, either restrict vertical motions or require awkward arm rotations to perform work above or below the nominal support height.

Common laboratory operations such as pipetting and 'emulsion breaking' however require repeated, unrestricted horizontal and vertical freedom of motion as various instruments are picked up and manipulated and set down. The 'payload' may indeed be trivial but the total weight of the operators cantilevered outstretched arm typically varies between three and ten pounds and self-supported can be exhausting over time, resulting in a disturbing number of injuries and lost workdays. Problems are compounded for activities utilizing even larger payloads than are used in laboratory tasks. There are countless such activities in numerous industries.

'Pipetting' and other medical and scientific operations, including countless surgical, dental and therapeutic procedures, could greatly benefit from having gravity effectively 'negated' for the practitioner by iso-elastic means that could also effortlessly parallel all the large and small motions of his or her human arm and wrist in three-dimensional space. Problems arise, however, in providing a comfortable, ergonomically appropriate connection between existing articulated support equipment and the dissimilarly articulated human arm, wrist, and/or hand.

The human arm is a biological miracle, but it is prone to fatigue, and ultimately to injuries, due to repetitive stress. What is needed is an agile supporting structure between it and an analogously jointed, lifting device, which can indefinitely preserve the unimpeded, multi-axis, angular agility of the human arm, forearm, wrist and hand. Further needed is a preferably lightweight, spring-powered, substantially frictionless mechanical arm, which uses no external power and, which fairly effortlessly follows the user's intended/hand arm positions while carrying the weight of his or her arm. It should preferably be highly iso-elastic (so it consistently lifts the selected amount of weight from the bottom to the top of its articulating range), and it should be of low inertial mass so it does not require much effort to move it along with rapidly up and down or lateral arm movements. It also preferably should include a 'centering' feature so it does not depart from the momentary selected position; and should be substantially frictionless to facilitate forearm rotations in pan, tilt and roll and spatial translations vertically, horizontally and towards/away-from the body of the user.

In summary, what is needed is a support apparatus that is spatially agile and can counter the weight of an outstretched human arm, wrist, and hand engaged in protracted tasks.

SUMMARY OF THE INVENTION

Illustrative embodiments of the invention provide an arm-supporting device pivotally attached to an agile lifting structure adapted to equipoise the weight of the human arm, wrist and/or hand. The lifting structure preferably contains one or more equipoising segments, such as spring-powered parallelogram lifting devices, with low-friction joints.

Illustrative embodiments of the apparatus, when attached to a fixed support apparatus analogous to that of the user's shoulder, extend through a plurality of positions paralleling those of the human arm and wrist. The apparatus preferably has an upwardly biasing force substantially countering the force of gravity, thereby facilitating protracted tasks preferably throughout the extent of human reach, while reducing or eliminating the human fatigue associated with self-support.

BRIEF DESCRIPTION OF THE DRAWINGS

For further detail regarding illustrative embodiments of the invention, reference is made to the detailed description provided below, in conjunction with the following illustrations.

FIGS. 7a and 7b respectively show illustrative uses of an arm support to support the forearm at mid-chest height and fully depressed at waist height, respectively, according to an illustrative embodiment of the invention.

DETAILED DESCRIPTION OF THE DRAWINGS

Figure 1:
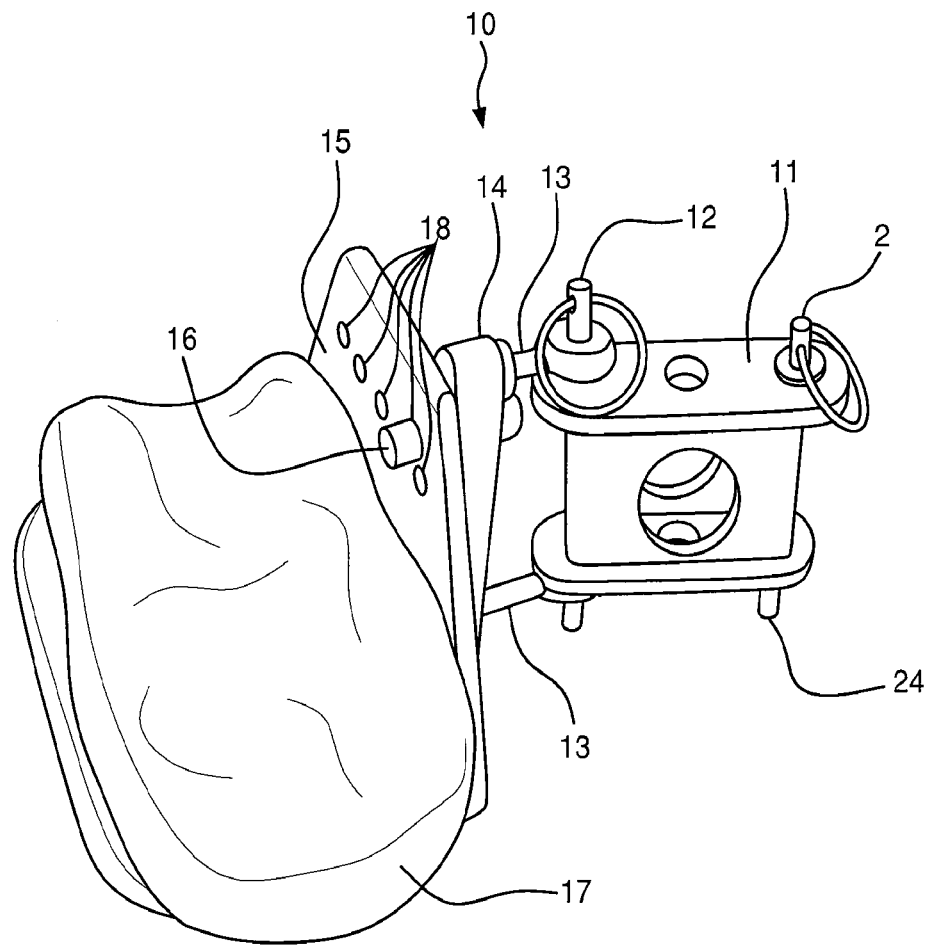
FIG. 1 is an isometric view of a human arm support including connecting hinge, pivotally connected support bracket and contoured armrest according to an illustrative embodiment of the invention.

FIG. 1 is an isometric view of human arm support 10 according to an illustrative embodiment of the invention. It includes connecting hinge 11, pivotally connected support bracket 15 and contoured armrest 17. Pin 24 connects hinge 11 to a mechanical arm at distal pivot location 2. Hinge 11, pivoting on axles 12 and 24 helps provide the angular freedom required by human wrist motions and cantilevers the human arm support laterally from the mechanical lifting arm 1 (shown in FIG. 2) to permit substantially unimpeded human arm function directly alongside the analogous functioning of arm 1.

A provision for angular adjustment of the arm support apparatus is preferably provided to axially bias the arm supporting shelf to help keep the human forearm aboard or positioned comfortably during various exertions.

Hinge pivot axle 12 captures ball rod ends 13 which are preferably adjustably attached to armrest support block 14. Armrest support bracket 15 pivots on axle 16 through bearings mounted within support block 15. Axle locating holes 18 enable selectable fore/aft balancing attitude for bracket 15. Contoured, padded armrest cushion 17 is attached to bracket 15. Its axial position can be trimmed using ball-rod-ends 13 to help prevent the resting human arm (not shown) from being dislodged by sudden lateral moves.

The mechanical lifting structure attached to embodiments of the inventive arm support preferably comprises a double section parallelogram spring arm (see FIG. 2), substantially frictionlessly jointed, including, starting at the proximal end: a hinge with one or more vertical pivots, a first parallelogram segment with four horizontal pivots, a central hinge with one or more vertical pivots, a distal parallelogram segment with four horizontal pivots and a distal vertical pivot. A single parallelogram arm may also be used. Various other hinges, pivots and fastening components may also be employed.

Figure 2:
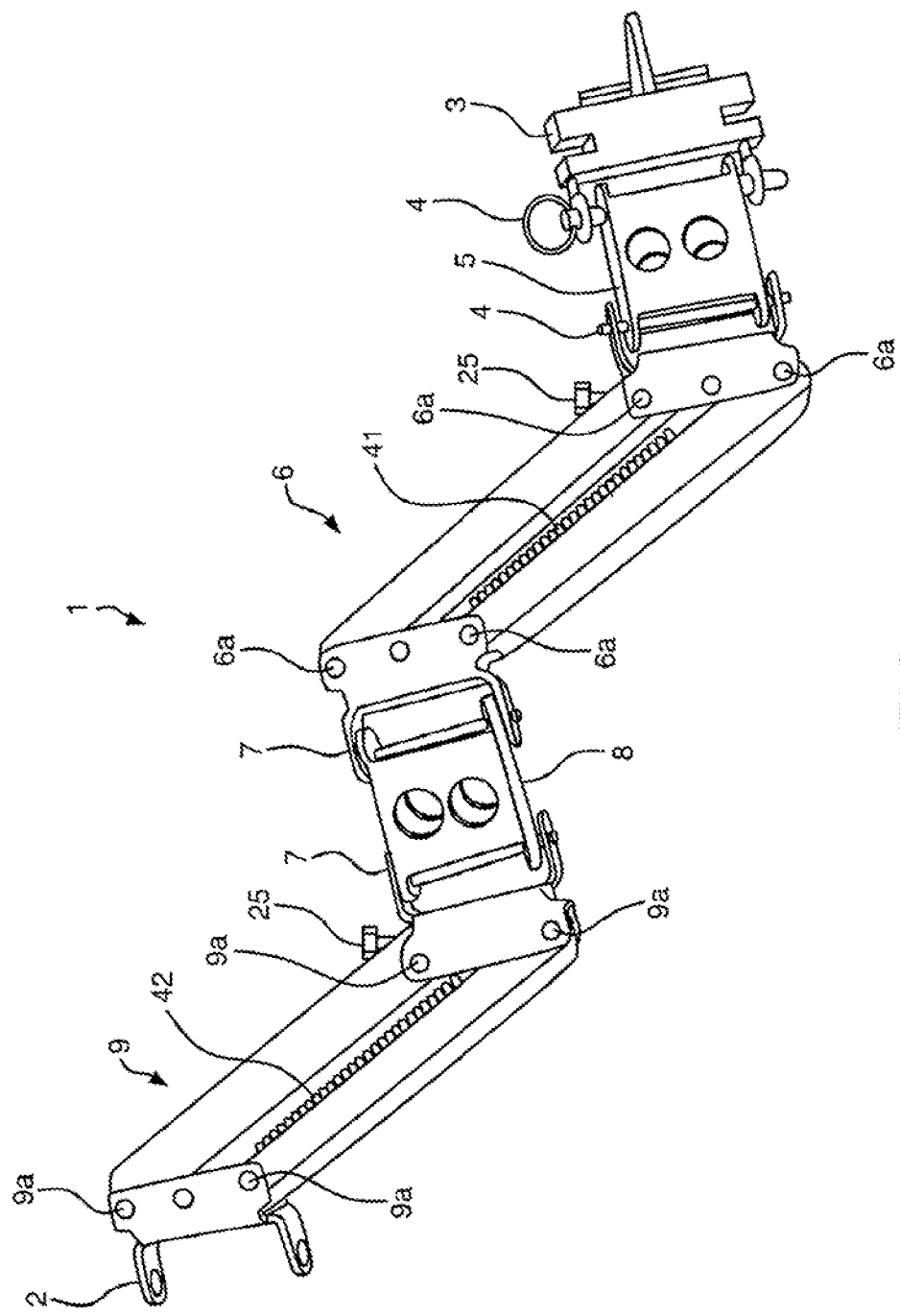
FIG. 2 depicts a mechanical support arm appropriate for use in conjunction with an inventive human arm support according to an illustrative embodiment of the invention.
Figure 16:
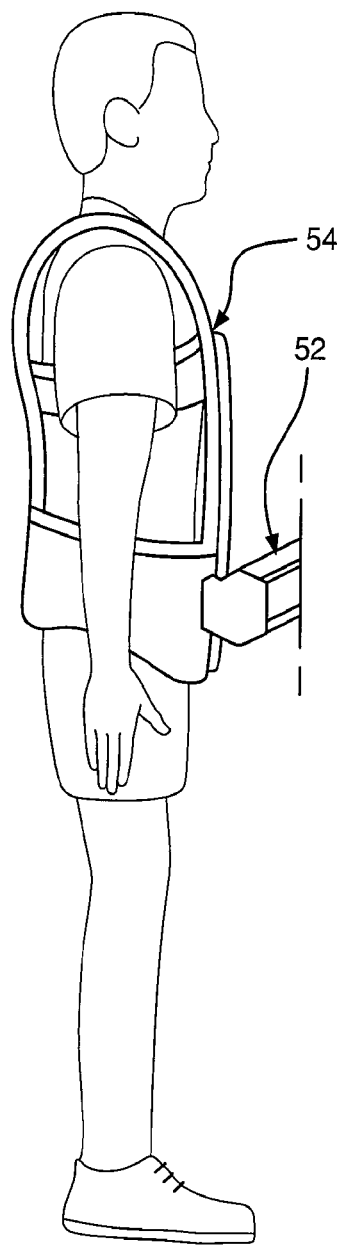
FIG. 16 depicts a portion of an arm support apparatus attached to a harness according to an illustrative embodiment of the invention.

FIG. 2 is an illustrative side view of a preferably iso-elastic mechanical support arm 1 adapted to lift a human arm support. Proximal connector 3 mounts to fixed supports 44 (shown in FIG. 8) or a support harnesses worn by an ambulatory user (an illustrative example of which is shown in FIG. 16). Hinge 5 and pivots 4 provide angular and lateral freedom analogous to that of the human shoulder. Proximal arm segment 6 pivoting on four horizontal axles 6a and distal arm segment 9 pivoting on axles 9a are biased upwardly by resilient mechanisms 41 and 42, the proximal terminations of which (not shown) are adjusted upwardly or downwardly by knobs 25 to alter the amount of effective lift at distal pivot location 2. In preferred embodiments of the present invention, arm segments 6 and 9, respectively, move and lift synchronously with, and analogously to, the human upper arm and forearm, while medial hinge 8 and pivots 7 provide angular functionality analogous to that of the human elbow.

Various spring powered 'equipoising' parallelogram arms, such as those employed to support and position payloads such as lamps, x-ray machines and dental equipment, can be employed in embodiments of the invention. Ideally the arm should be iso-elastic. These arms rely to a greater or lesser extent on friction to retain a selected angle or position, but do not necessarily provide consistent lift throughout the entire angular excursion of the parallelogram links. Arms that also may be appropriate include those described in applicant's U.S. Pat. No. 4,017,168 (Re. 32,213), the diagrams of which are incorporated herein by reference. Applicant's U.S. Pat. No. 5,360,196, diagrams of which are also incorporated herein by reference, provides examples of iso-elastic arms that will be suitable for use in illustrative embodiments of the invention. These arms produce an iso-elastic lifting range by countering the fixed weight of the assembly they support with nearly constant payload buoyancy.

Arms described in applicant's recent application no. PCT/US2006/014036 or U.S. application Ser. No. 11/403,731, Equipoising Support Apparatus, incorporated herein by reference, are also suitable for use with illustrative embodiments of the invention. The application describes a variety of single-spring geometries employing cams or cranks to dynamically improve lifting consistency and range of parallelogram articulation. The adjustment mechanisms described in the application can be employed in embodiments of the present invention, and can be user-adjusted.

Equipoising arms, such as those described in the patents/applications mentioned above can provide the desired iso-elasticity and lateral and vertical range. Features, such as knob-adjusted payload adjustment to float the range of human arm weights from the lightest to the heaviest, and analogous 'shoulder, upper arm, elbow and forearm' segments can be advantageous to illustrative embodiments of the invention.

It is noted that other tensioning mechanisms can be used in place of the springs referred to herein.

Figure 3:
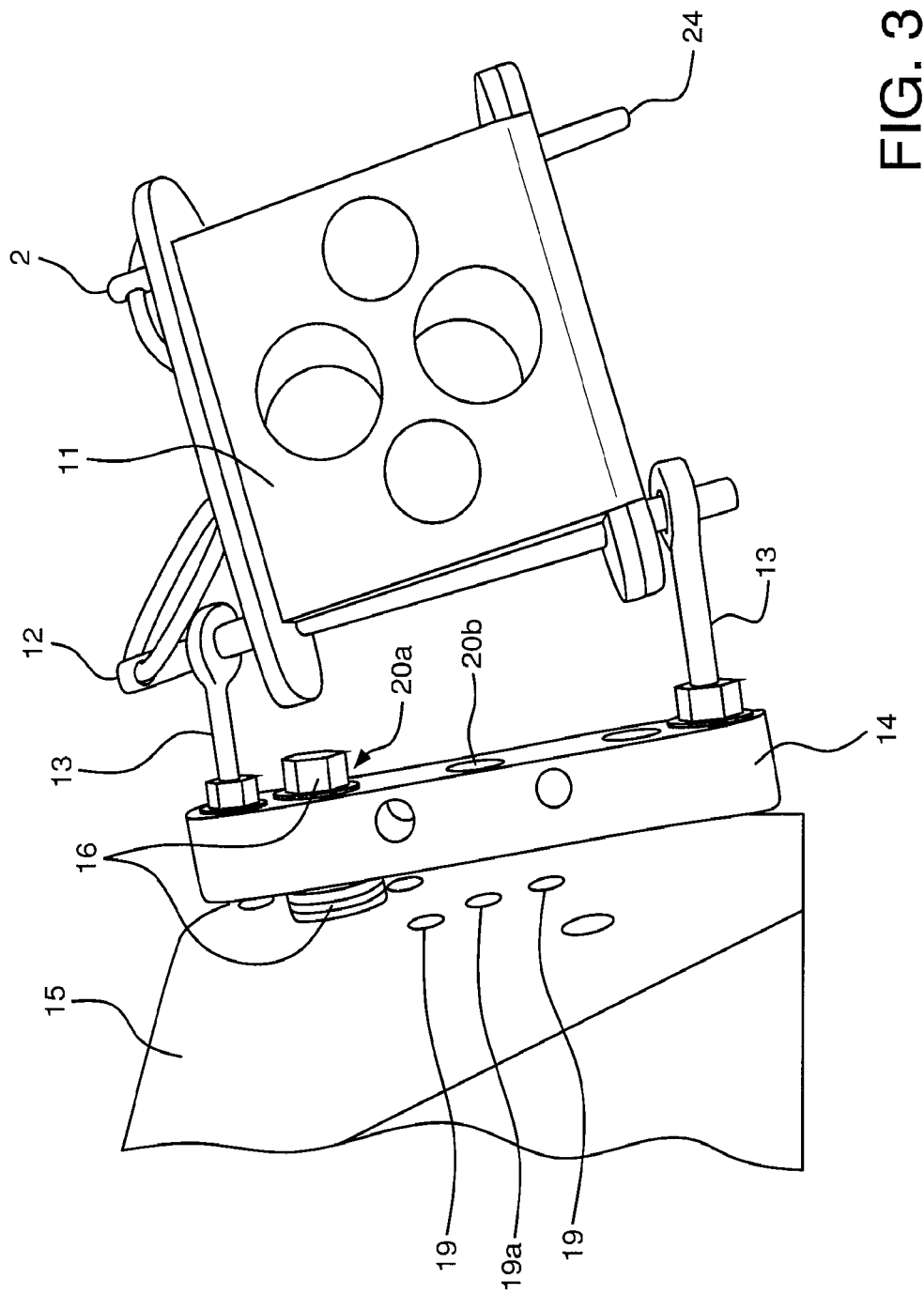
FIG. 3 depicts a two-axis pivoting connection between the final hinge and the human arm support bracket, including adjusting mechanism for angular displacement of one axis according to an illustrative embodiment of the invention.

FIG. 3 depicts a two-axis pivoting connection between hinge 11 and arm support bracket 15, including adjusting mechanism 13 for angular displacement of one axis according to an illustrative embodiment of the invention. Ball-rod-ends 13 are shown in detail to illustrate the range of angular displacement possible between axle 12 and armrest support block 14. (Note that arm support hinge 11, shown here at an angle to arm support bracket 15, would generally be level with it.) Axle 16 pivots armrest bracket 15 with respect to support block 14 at a raised location 20a to provide pendulum, bottom-heavy mounting above the center of mass of the resting human arm. Bearing hole location 20b and hole 19a (seen positioned adjacently in vertical row of holes 19), could provide a lower, more neutral balance position for axle 16.

The horizontal arm support pivot can be adjusted with respect to the distal arm end in one or more directions. As the operator may desire, the horizontal arm support apparatus pivot can be positioned above, below or level with the arm resting surface. The pivot can be positioned level with the horizontal center of gravity to provide little or no angular bias, or can be displaced above, or below the center of gravity of the arm to yield a selectable bias for the arm to remain tilted as desired. This pivot can also be adjusted substantially horizontally to provide a bias for the forearm to be angled slightly up or down as the work dictates, or to rebalance fore-and-aft for comfort, in regard to the center of the human arm's intrinsic mass.

Figure 4A:
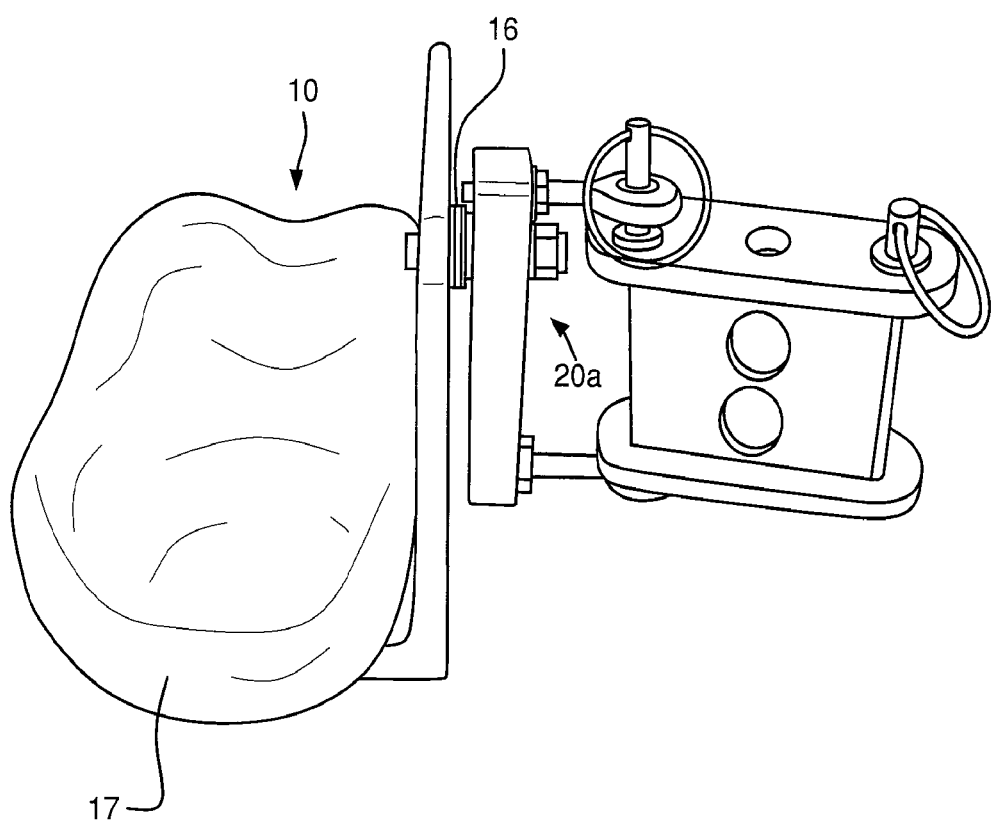
FIGS. 4a and 4b show two selectable, vertically displaced pivot locations for the arm support bracket which would provide, respectively, either a slightly bottom heavy or a neutral balance for the human forearm (not shown) on the contoured armrest surface according to illustrative embodiment of the invention.
Figure 4B:
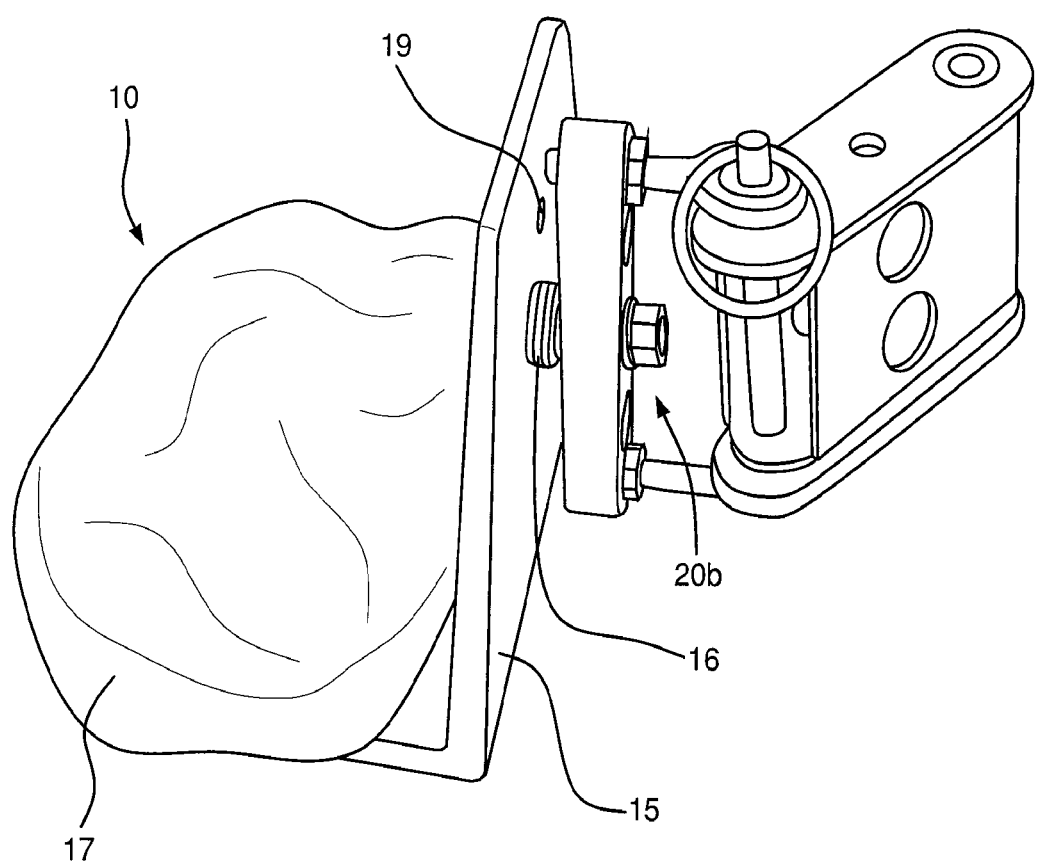

FIGS. 4a and 4b show another view of the two selectable, vertically displaced pivot locations for arm support bracket 15 which provide, either a slightly bottom heavy (FIG. 4a) or a neutral balance (FIG. 4b) for a supported human forearm (not shown) according to illustrative embodiments of the invention. Axle 16, mounted at location 20a is above the nominal center-of-mass of the forearm (not shown) as it would rest on pad 17, whereas location 20b (FIG. 4b) is closer to the center-of-mass and would more neutrally balance the forearm, and thus would require little or no effort to tilt the arm around axle 16 as the working need dictates.

Figure 5A:
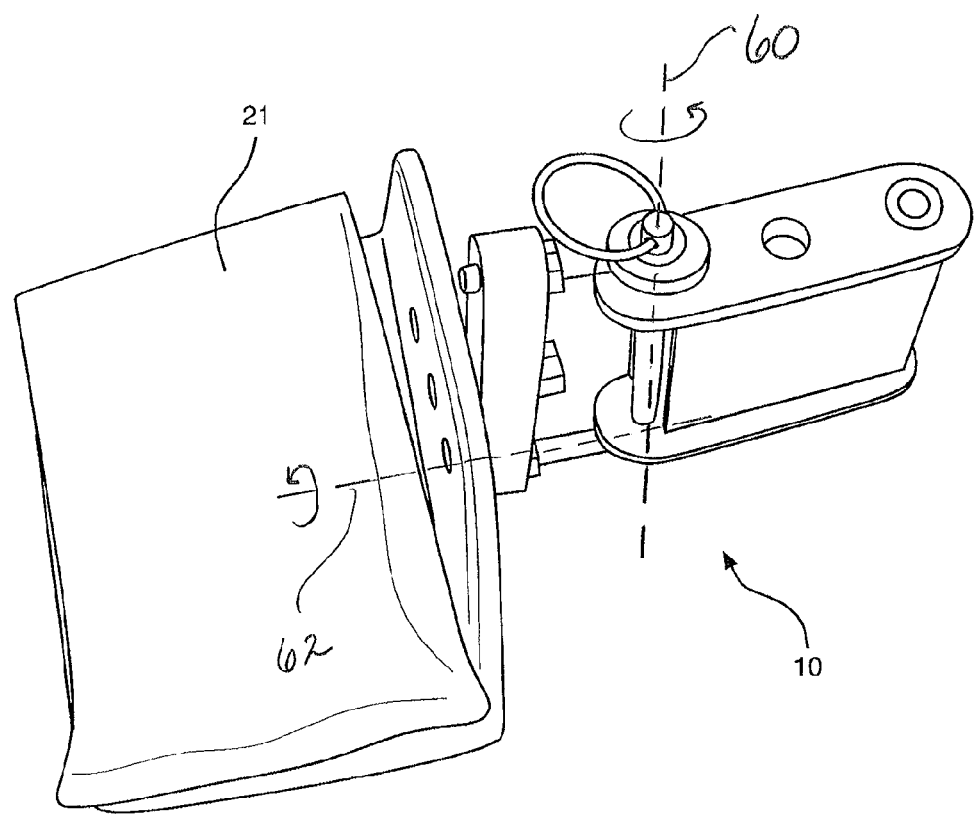
FIG. 5a shows a compliant beanbag-type rest surface according to an illustrative embodiment of the invention.
Figure 5B:
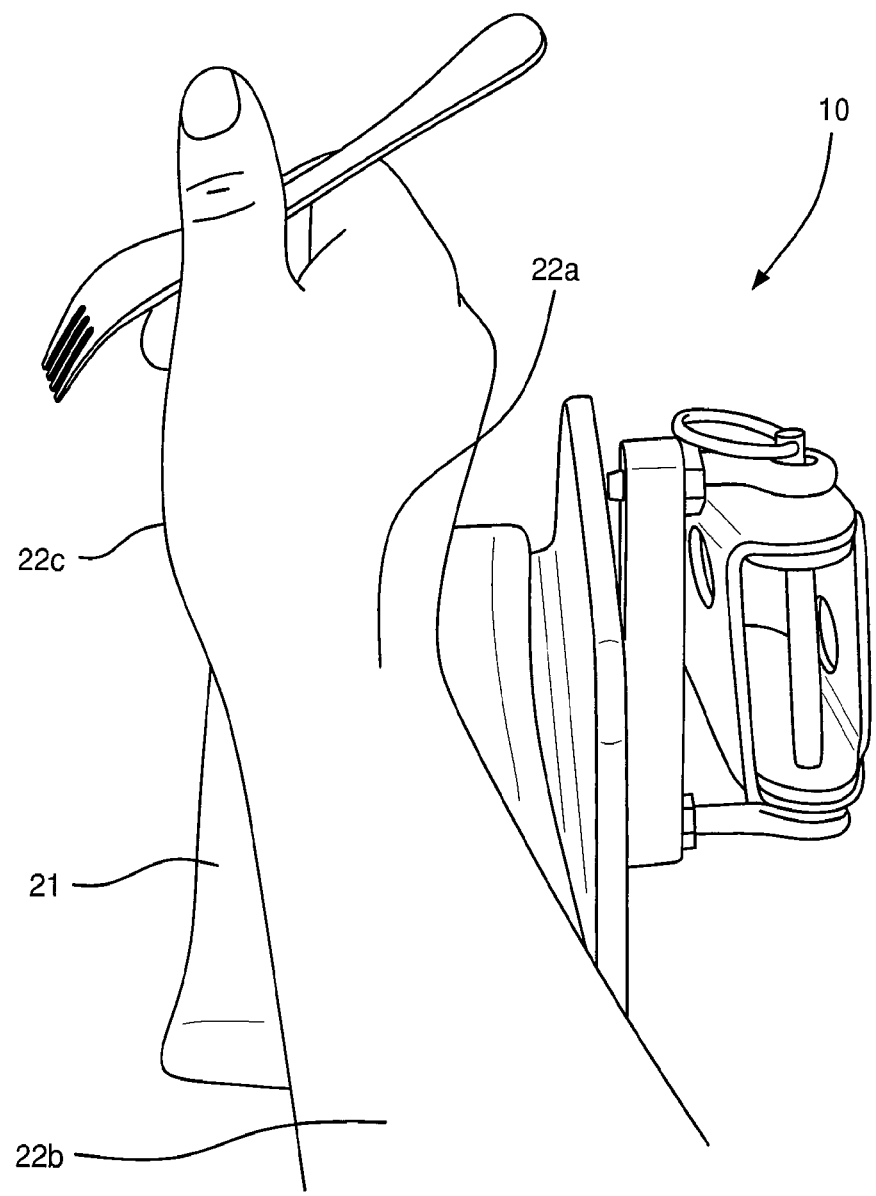
FIG. 5b shows the rest surface of FIG. 5a in use according to an illustrative embodiment of the invention.

FIG. 5a shows a beanbag-type armrest pad 21 and FIG. 5b shows armrest pad 21 in use to compliantly facilitate rotation between human forearm 22b and wrist 22a and/or heel of hand 22c according to an illustrative embodiment of the invention. Beanbag 21, containing, for example, buckwheat, flax seeds, beans, plastic balls or other appropriate filler material, provides a compliant surface that can accommodate torsional rotation between wrist and elbow (not shown) due to the twisting range of the radius and ulna forearm bones while promoting the continuing circulation of blood and lymphatic fluids throughout the forearm. The filler material allows the pad to immediately conform to any new arm or hand position. This compliance functions analogously to the "roll" axis of a gimbal in a nautical or camera application. Human arm support 10 transparently permits arm 22 to 'pan' (rotate around a vertical axis, such as axle 60) and 'tilt' (rotate around a horizontal axis, such as axle 62, perpendicular to the long axis of arm 22). Effective freedom in 'roll' however is obtained by the shifting of the internal filler of the beanbag at the heel-of-hand location vs. the more stationary forearm location, in order to accommodate various task-related hand angles. Embodiments that only require forearm support may employ other conventional methods and materials to provide individualized comfort, including microwaveable beanbag versions and vacuum immobilized versions that retain shaped impressions, and interchangeable, custom-molded pads adapted to comfortably support the forearms of various users for long periods of arm-extending work.

Figure 6A:
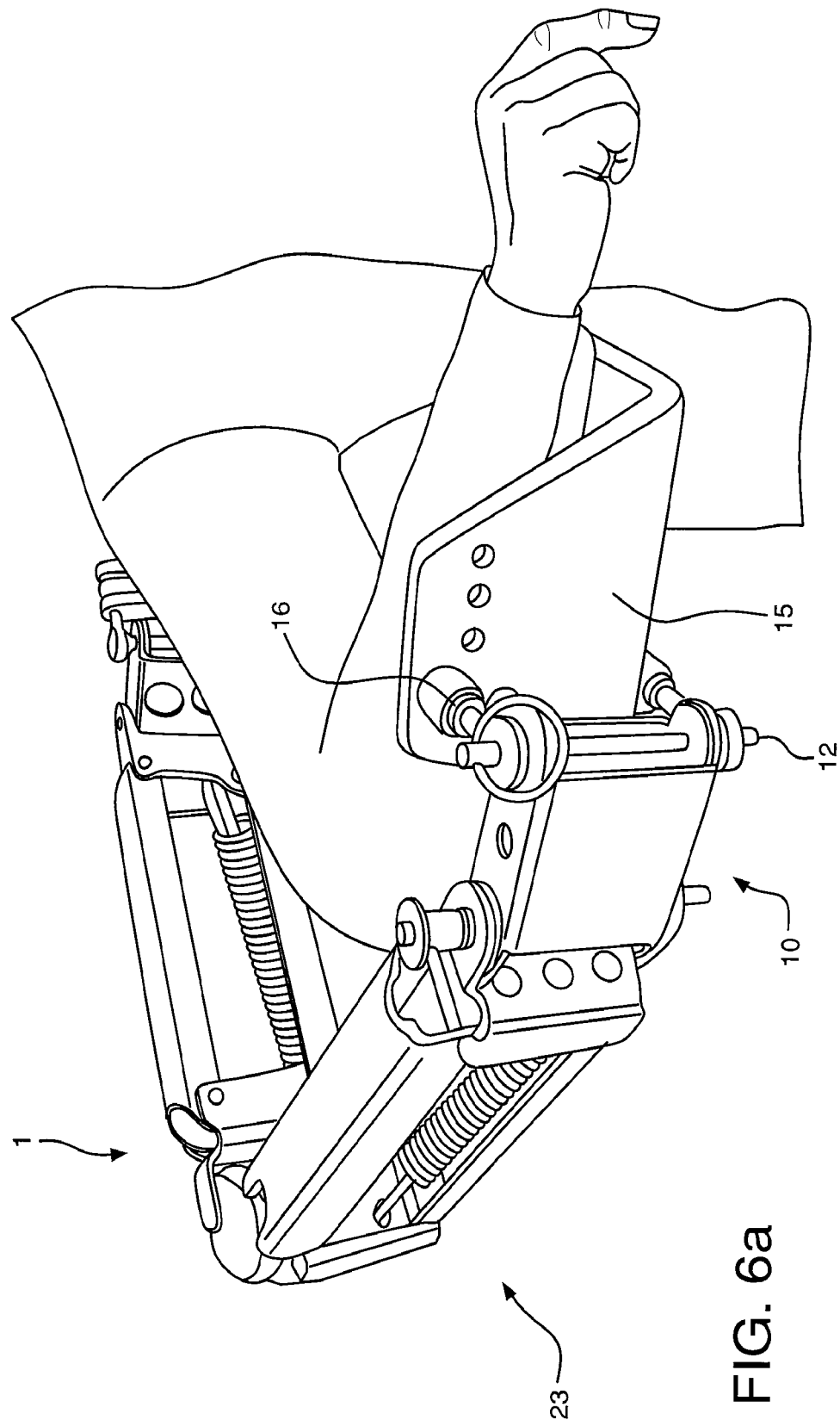
FIGS. 6a and 6b show illustrative uses of the invention supporting a human forearm, respectively, tucked back toward the chest and fully extended, to display the angular agility of the arm support as it parallels human arm positions according to an illustrative embodiment of the invention.
Figure 6B:
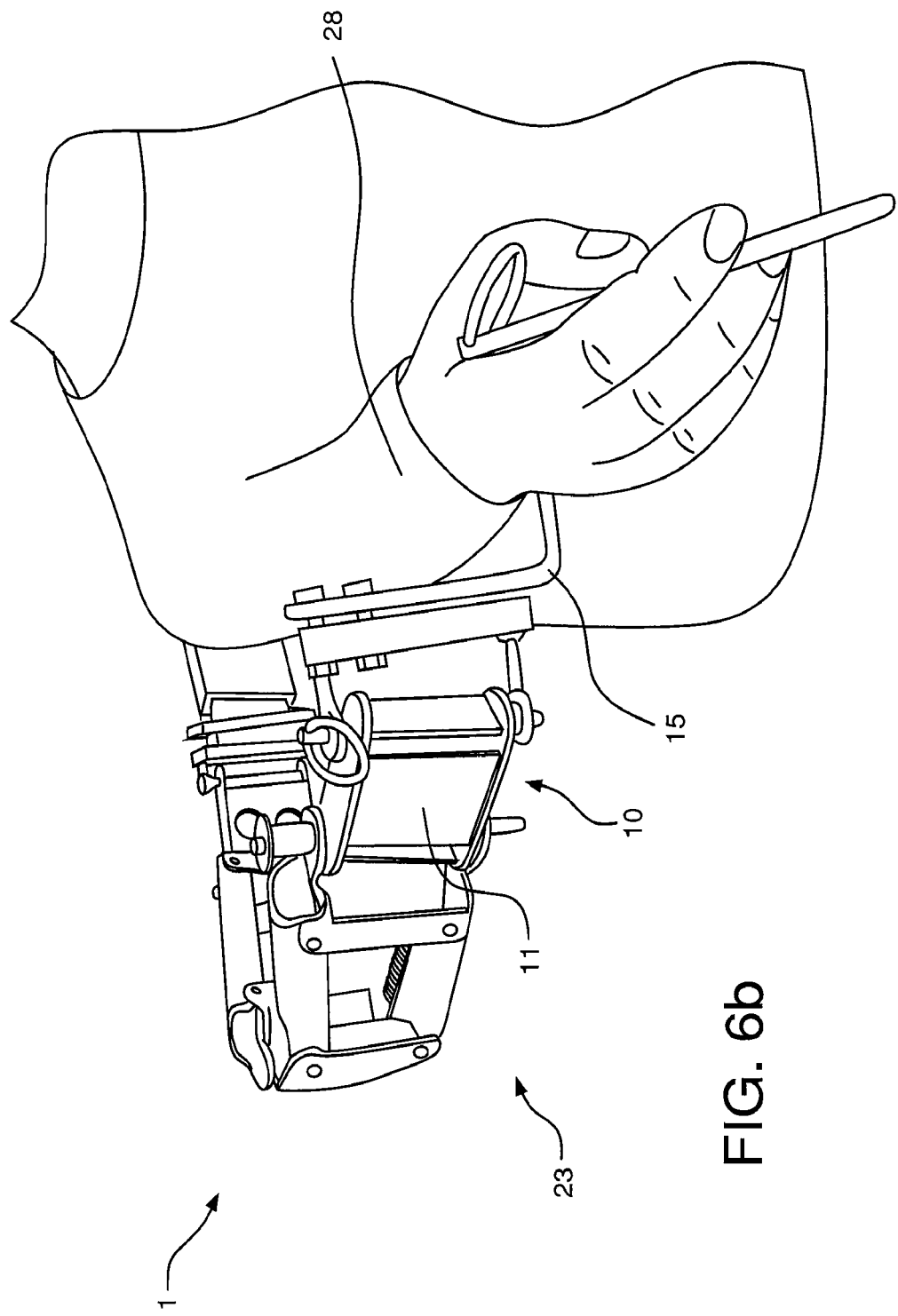

FIGS. 6a and 6b show two different lateral and angular displacements of an articulated human arm support apparatus 23, consisting of human arm support 10 moveably connected to mechanical arm 1 and carrying human forearm 28, respectively tucked back toward the chest, and fully extended—illustrating thereby the angular agility of arm support 10, and the two-axis angular isolation between arm support bracket 15 and mechanical lifting arm 1 provided by hinge 11 and pivots 12 and 16.

Figure 7B:
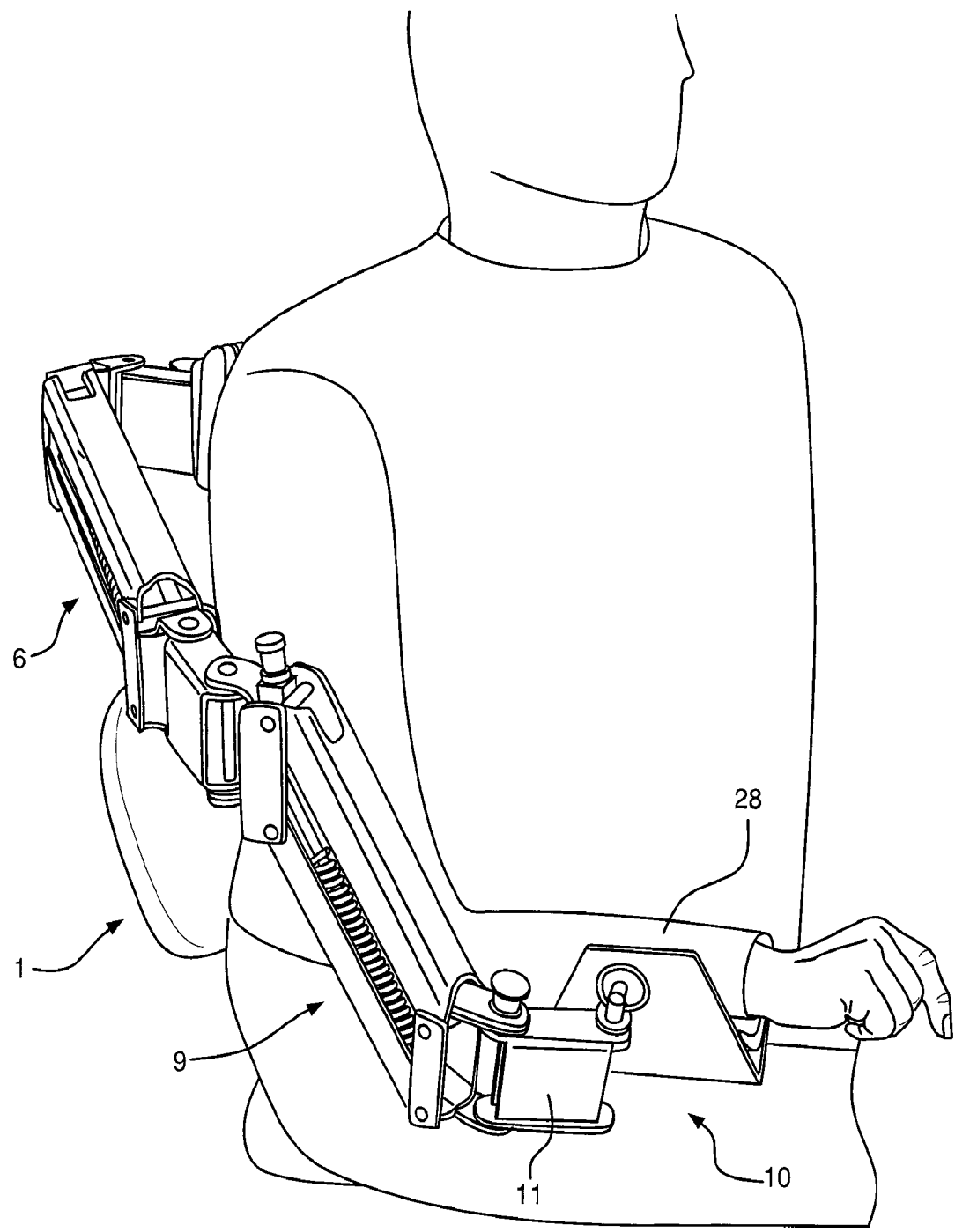

FIGS. 7a and 7b show another vector of motion of the Iso-elastic mechanical arm 1 combined with arm support 10 to carry a human forearm 28 respectively at mid-chest height, and at waist height with the arm against the body, according to an illustrative embodiment of the invention. As seen in FIGS. 7a and 7b, the substantially iso-elasticity and reduced friction pivots of arm 1 allow upper parallelogram arm segment 6 and forearm parallelogram segment 9, to rise and fall synchronously (at similar angles) throughout the articulation of arm 1 from its lowest to highest positions—while hinge 11 remains horizontal or at the same angle with respect to the horizontal throughout.

Figure 8:
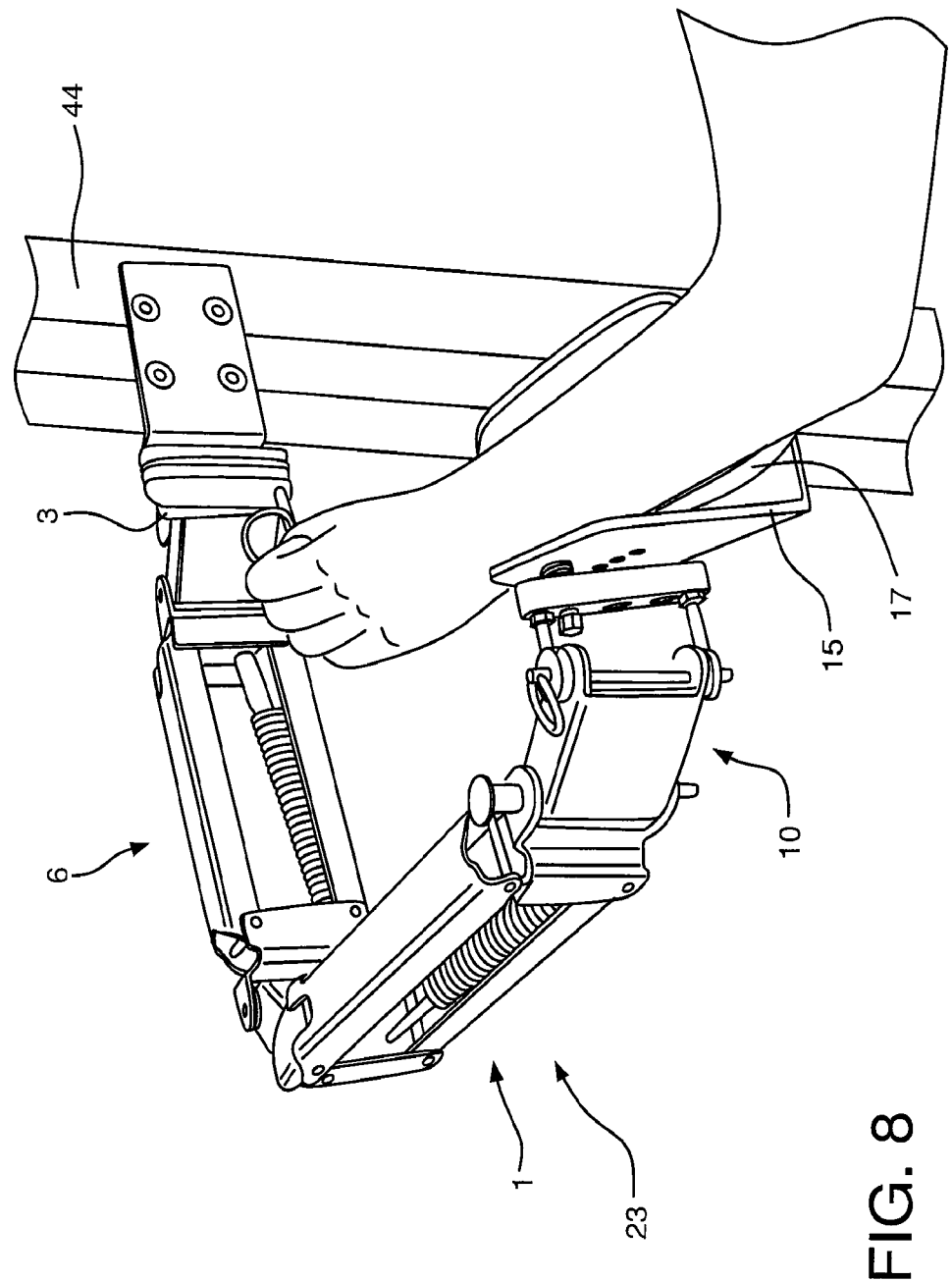
FIG. 8 shows an operator oppositely positioned as compared to the position depicted in FIGS. 7a and 7b using a human arm support according to an illustrative embodiment of the invention.

FIG. 8 shows, according to an illustrative embodiment of the invention, a deployment position of the combined articulate human arm support 23 opposite to that shown in FIGS. 7a and 7b. The illustrative arm support apparatus 1 is not disposed contiguously alongside the user's arm as is the case in FIGS. 7a and 7b. Instead, mechanical arm segments 6 and 9, armrest bracket 15 and pad 17 are positioned in front of the worker. Although the typical preferred position of use of mechanical arm 1 would be alongside one of the worker's shoulders so that the mechanical arm 1 roughly parallels the human upper arm and forearm in both position and angle movement; the use of the arm support as shown in FIG. 8, may also provide a similar and complementary range of angular and spatial positions even though mounted distantly from the human shoulder. This arrangement may be useful, for example if the most suitable mounting location is on a table, such as in a laboratory where a task such as pipetting is to be performed. For tasks performed at a table, workbench, desk, or the like, one or two mechanical arms can be mounted on a chair.

Figure 9A:
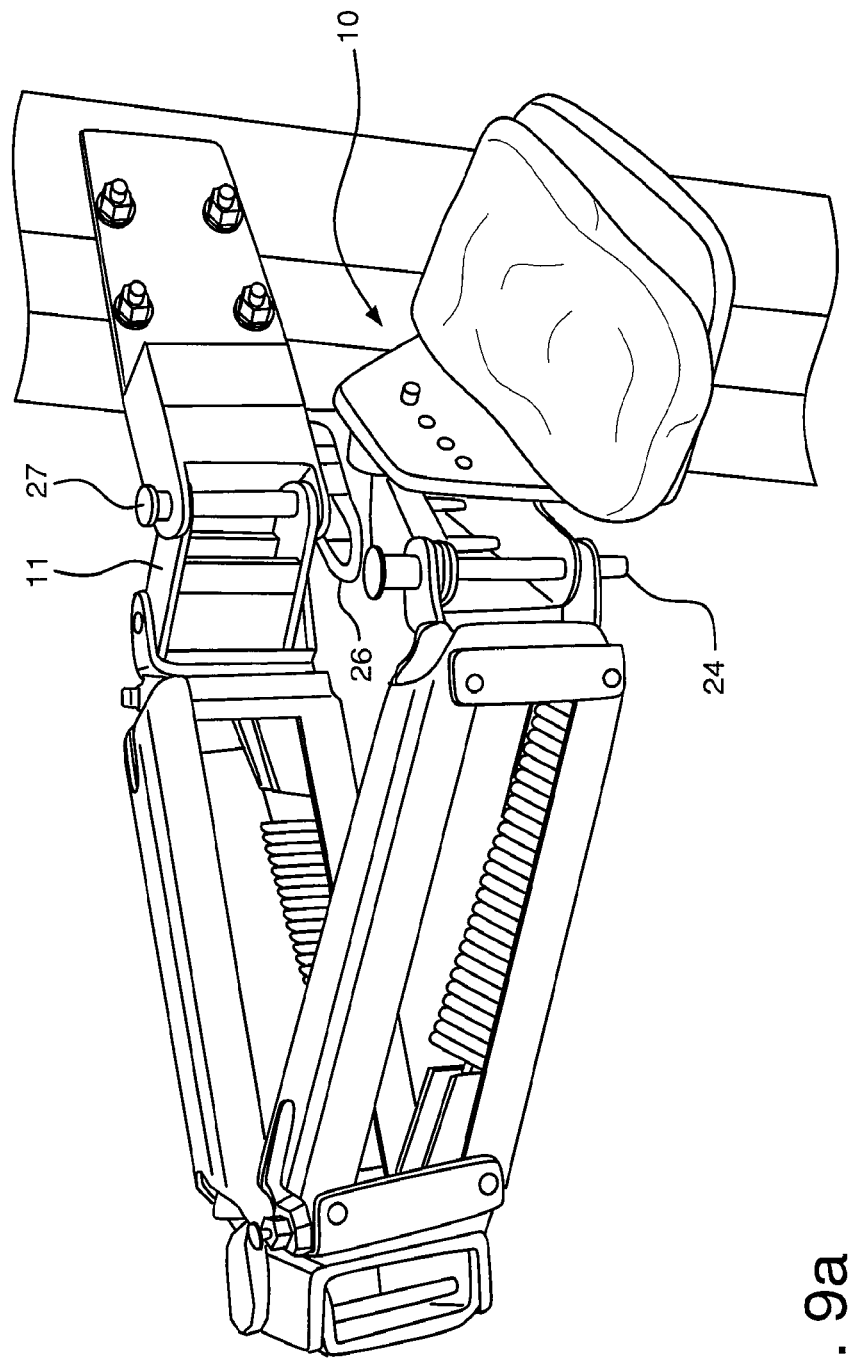
FIG. 9a shows a human arm support 'docked' at a position off to the side of the work area, at a level fixed slightly below mid-height of the full vertical range of the apparatus according to an illustrative embodiment of the invention.
Figure 9B:
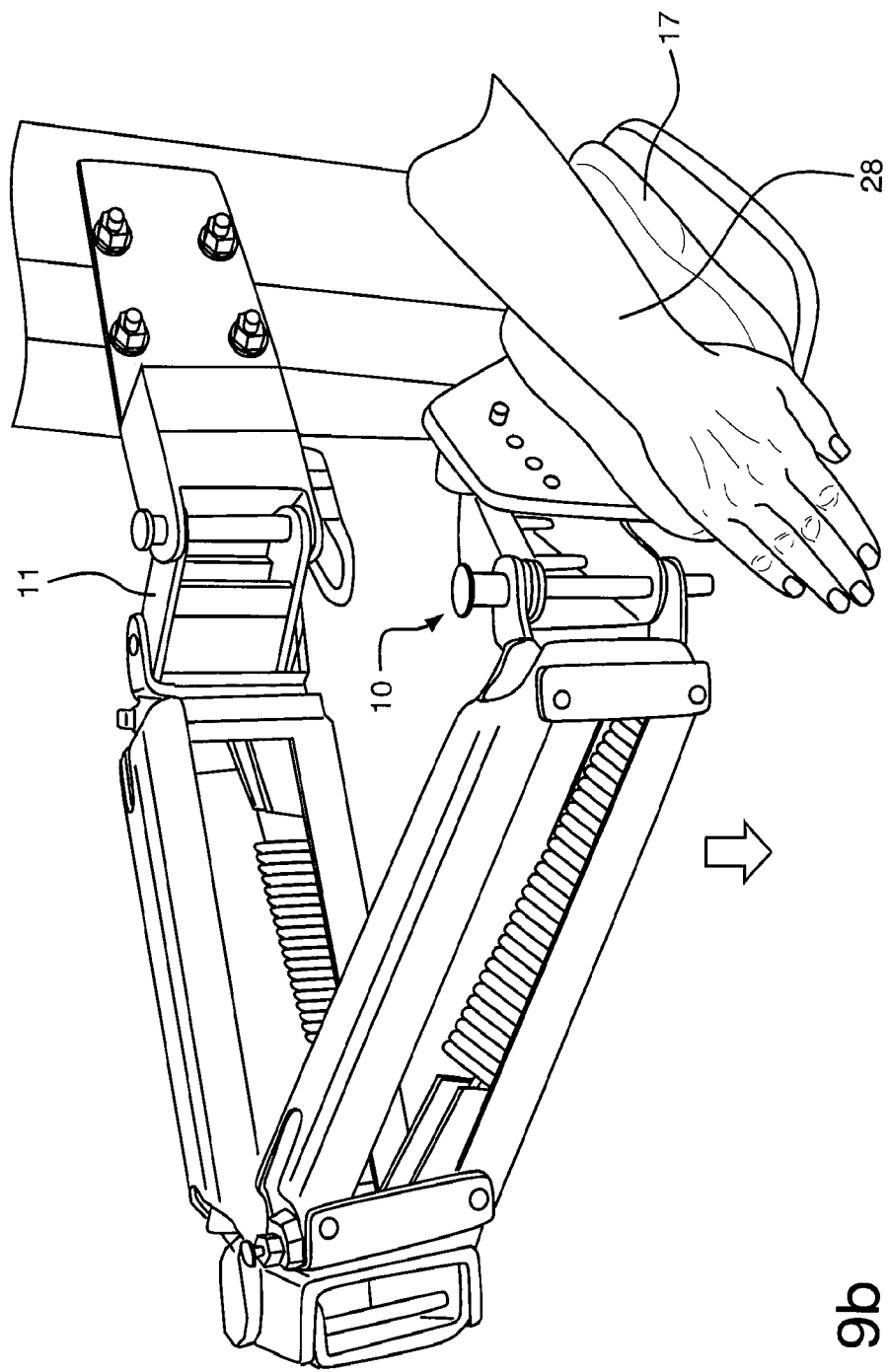
FIG. 9b illustrates the undocking procedure as the user's arm is set upon the armrest surface and lowered just enough to disengage the docking mechanism according to an illustrative embodiment of the invention.

FIG. 9a shows human arm support 10 fixedly 'docked' at a position off to the side of the work area and slightly below mid-height. In this embodiment, docking ring 26 associated with hinge 11 and pivot pin 24 engages the bottom of proximal hinge pin 27. FIG. 9b illustrates the un-docking procedure as the user's forearm 28 is set upon the armrest surface 17 and lowered just enough to disengage docking elements 26 and 27.

Embodiments of the invention may also provide for mounting the human arm support apparatus suspended from, perched above, or cantilevered alongside the mechanical arm, so that the supported human arm and/or heel of hand is disposed either above, below or alongside the analogously jointed equipoising arm—or extending back to the worker's arm or hand from a different location, as workplace requirements and spatial obstructions may dictate.

Figure 10A:
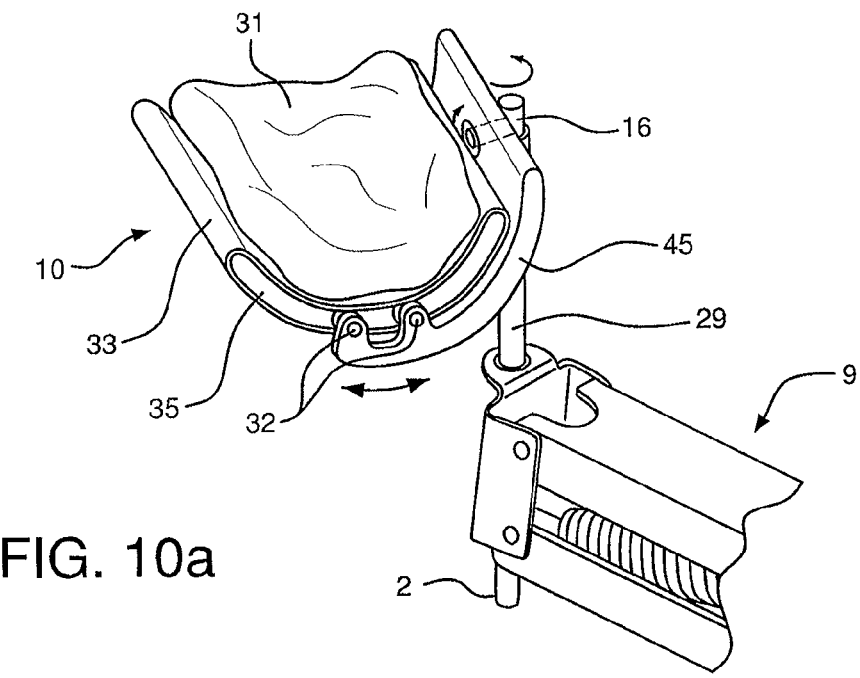
FIGS. 10a and 10b show a human arm support apparatus mounted respectively above and below the distal end of the equipoising lifting arm to accommodate various work environment obstructions without interference according to an illustrative embodiment of the invention.
Figure 10B:
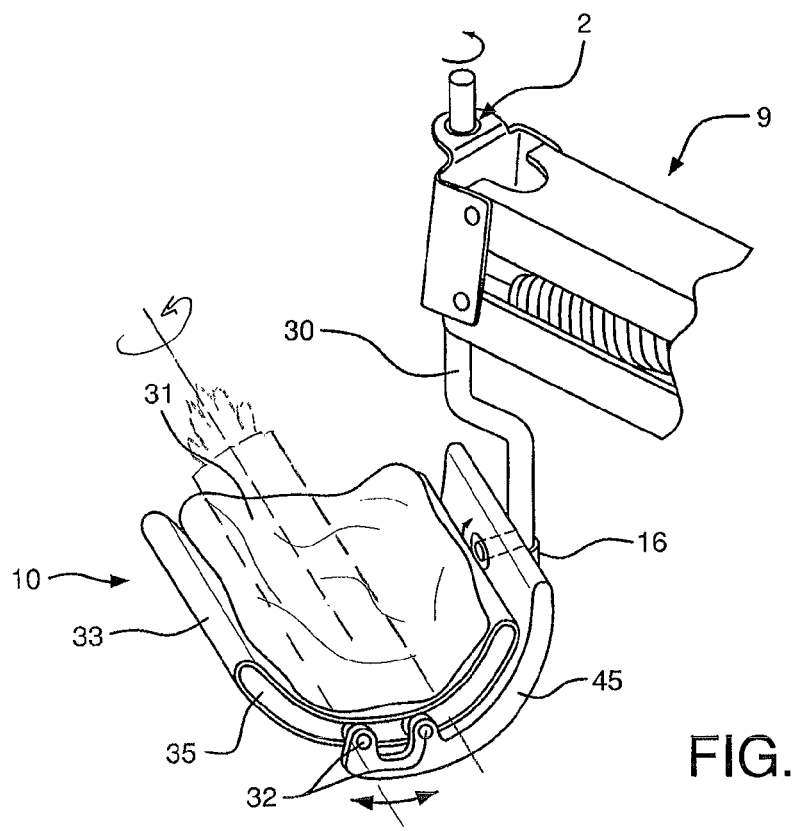

FIGS. 10a and 10b show other illustrative embodiments of the human arm support apparatus 10 mounted, respectively above and below the distal pivot 2 of the equipoising lifting arm to accommodate various work environment obstructions without causing interference, and as alternatives to the mounting of support brackets laterally adjacent to armrest bracket 14. These arrangements may facilitate work in areas that have limited lateral room but have space available below or above the optimal range of positions for the human arm. They also can allow the human arm or parts thereof to pass over or under mechanical arm 1. In FIG. 10a, elevated mounting pin 29 is rotatably mounted in pivot location 2 at the distal end of arm segment 9 and is cross-drilled above to contain the bearings for axle 16. In FIG. 10b, suspended mounting pin 30 is likewise rotatably mounted in pivot location 2 and is cross-drilled below to contain the bearings for axle 16. As shown in FIG. 10b, mounting pin 30 may have a non-linear shape. It may be curved or jogged to accommodate various uses.

In each of FIGS. 10a and 10b, axle 16 is pivotally attached to track roller support 45. Track rollers 32 are positioned by support 45 to engage roller track 35 (optional opposite roller track and rollers are not visible), which are attached to roll plate 33 which support padded armrest 31. Other rolling mechanisms can be used that allow padded armrest 31 to "roll" about an axis substantially parallel to the user's forearm. An illustrative example of such an axis is shown in FIG. 10b. For example, ball bearing mechanisms may be used instead of roller or wheel mechanisms.

In an illustrative embodiment of the invention, approximately plus/minus 25 degrees of reduced friction or frictionless axial roll for the resting forearm and/or heel of hand is provided, as workplace hand manipulations may require. Illustrative roll ranges are about 15° to about 35°, and about 20° to about 30°. Analogously to the roll-axis bearing of a gimbaled camera or tool support, these roll plates provide a third degree of rotational freedom that can exceed the roll-axis compliance of the beanbag armrests of FIGS. 5a and 5b or can provide an additional or substitute means of roll.

The arm support apparatus may include a simple padded rest for forearm support, or separate surfaces, pivotally interconnected around one or more axes, to permit relative angular movement between forearm and wrist (and/or heel-of-hand). In another illustrative embodiment of the invention, the rotational freedom between supported forearm and wrist (or heel-of-hand) is partially achieved by a support structure comprising beanbags or buckwheat-filled bags or other compliant media, such as longitudinally disposed, air-filled, toroidal cushions. This can allow the arm and hand to rotate without lifting from, or sliding on the resting support.

Embodiments of the invention may also provide additional articulation between the arm-supporting portion of the structure and the hand-supporting portion such that the human forearm and hand may be angularly exercised relative to one another in as many as three roughly perpendicular axes without undue restriction or external influence.

Figure 11:
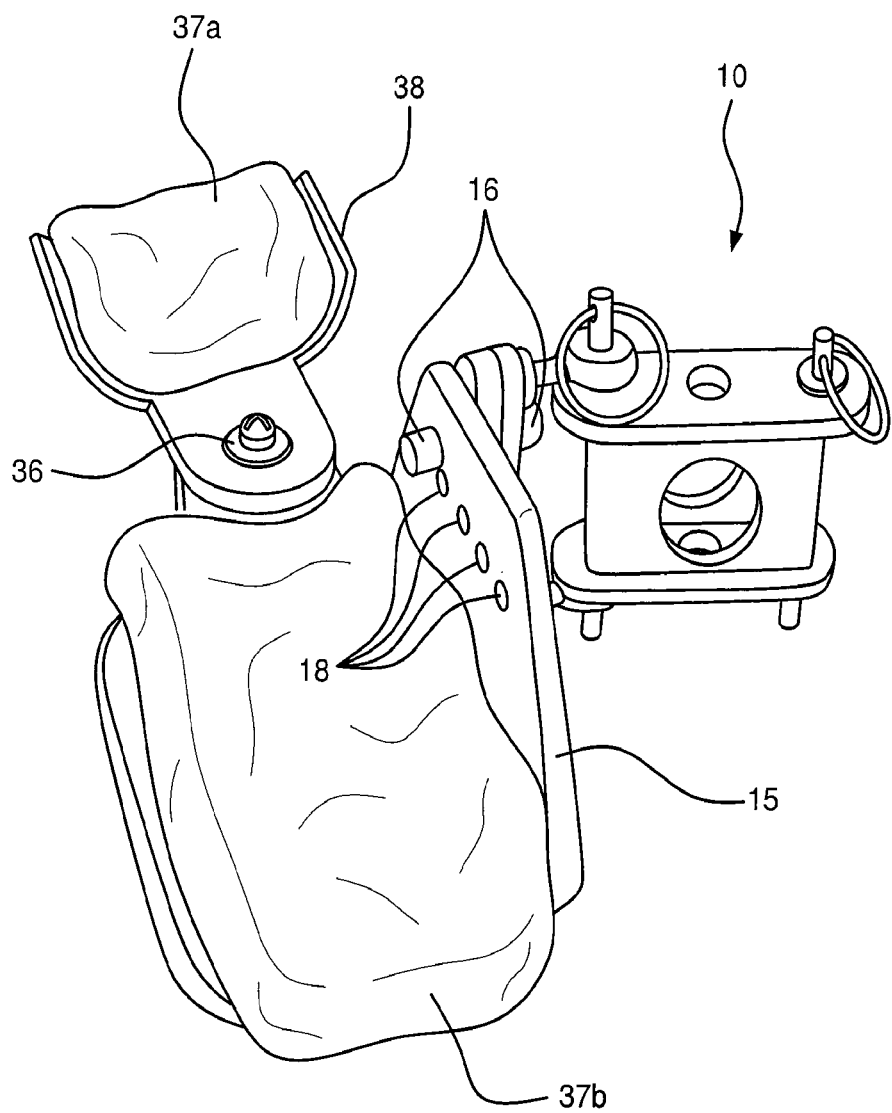
FIG. 11 shows another illustrative embodiment of the invention with separate rest surfaces for forearm and heel-of-hand connected by an axis pivot (preferably located below the wrist joint) which permits the heel of the hand to independently rotate vs. the forearm.

FIG. 11 is an isometric view of another illustrative embodiment of the human arm support 10 with padded hand-rest surface 37a held by curved support bracket 38 pivotally interconnected by a preferably and substantially vertical axis pivot 36 (preferably located directly below the wrist joint), which permits the heel of the hand thereon to independently rotate side-to-side vs. the forearm resting on forearm rest 37b held by armrest support bracket 15. In this embodiment, pivot axle 16 which suspends armrest support bracket 15 is located at a point where the weight of brackets 38 and 15, pads 37 and 37b and the supported hand and forearm is substantially balanced so as to seek a desired work position. The desired work position will often but not always be substantially horizontal. This is accomplished by displacing pivot axis 16 to an appropriate location hole selected from row 18. Note that continuous adjustments as well as selectable holes are contemplated in preferred embodiments to alter both vertical and horizontal centers of balance.

Figure 12A:
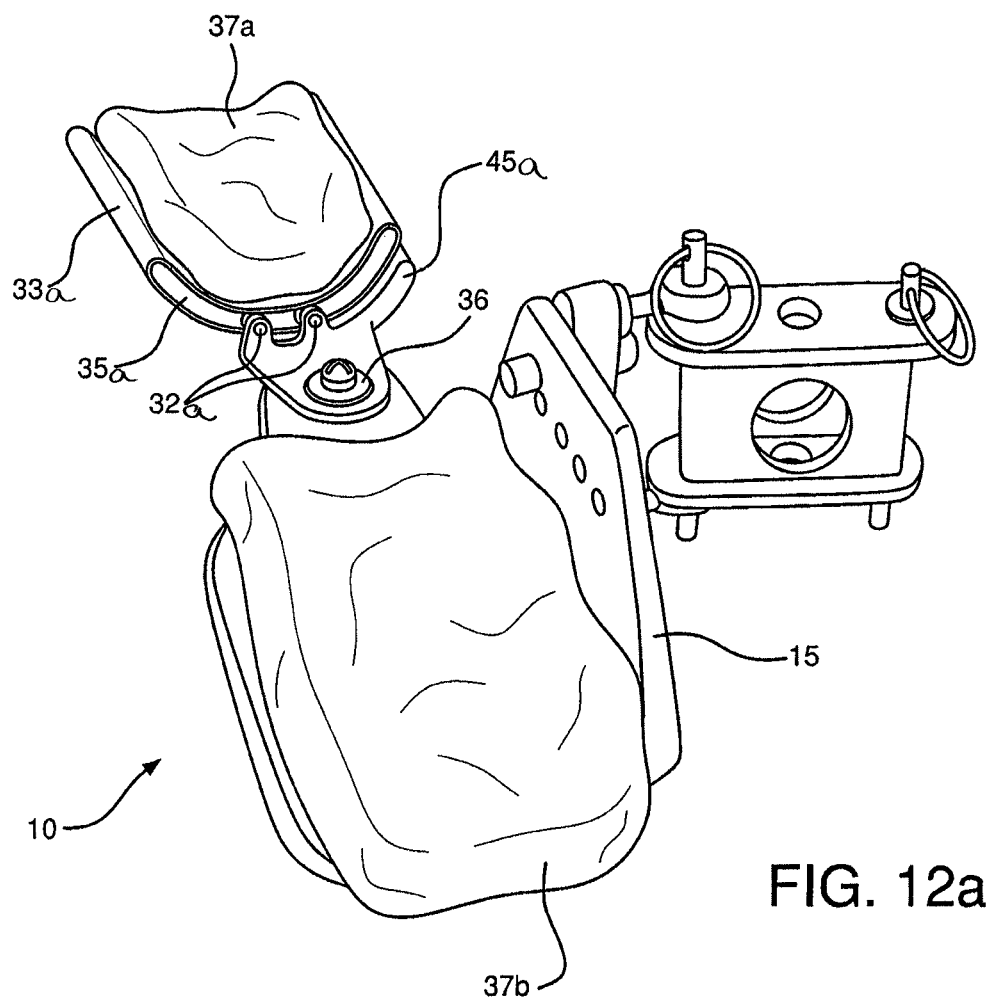
FIGS. 12a and 12b show two illustrative embodiments of the invention that include curved, tilting rest surfaces, permitting rotation with the resting forearm and/or heel of hand.
Figure 12B:
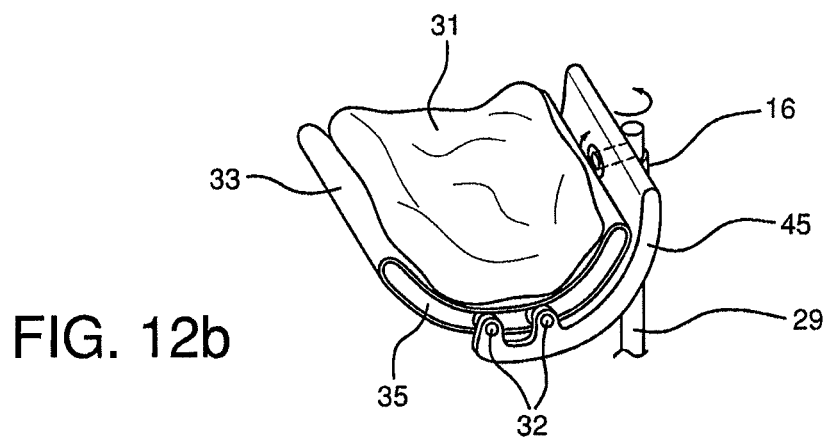

FIGS. 12a and 12b show illustrative embodiments of the human arm support 10 of FIG. 11 that include semi-cylindrical, or otherwise curved, tilting roll-plates 33a, 33 permitting rotation of the resting heel-of-hand and the forearm without lifting from or sliding on the resting surface. Roll plate 33 contains roller track 35a, 35, engaged with support 45a, 45, which accommodates track rollers 32a, 32, allowing roll plate 33 to move arcuately, preferably to plus/minus 25°. Illustrative roll ranges for roll plate 33 include about 15° to about 35°, and about 20° to about 30°. Track rollers can also be positioned on the far side but are not visible. The embodiment of FIG. 12a enables additional rotation around vertical axis 36, which pivotally connects roll-plate track roller support 45 to armrest support bracket 15. Hand rest pad 37a is therefore capable of motion in two perpendicular axes relative to forearm support pad 37b resting on support bracket 15 in order to facilitate complex hand motions with continuous individual support for heel-of-hand and horizontal centers of balance.

FIG. 12b shows a tilting roll plate to permit the forearm, either together with or separate from the heel-of-hand, a greater degree of rotation than any fixed pad (or beanbag) support. Armrest pad 31 can be configured to accommodate only the forearm or can allow the forearm and heel-of-hand to rest on it. Armrest pad 31 can be individually molded to fit a wide gamut of arm sizes and shapes, or custom fitted by means such as of microwaveable or vacuum-set beanbags.

Figure 13:
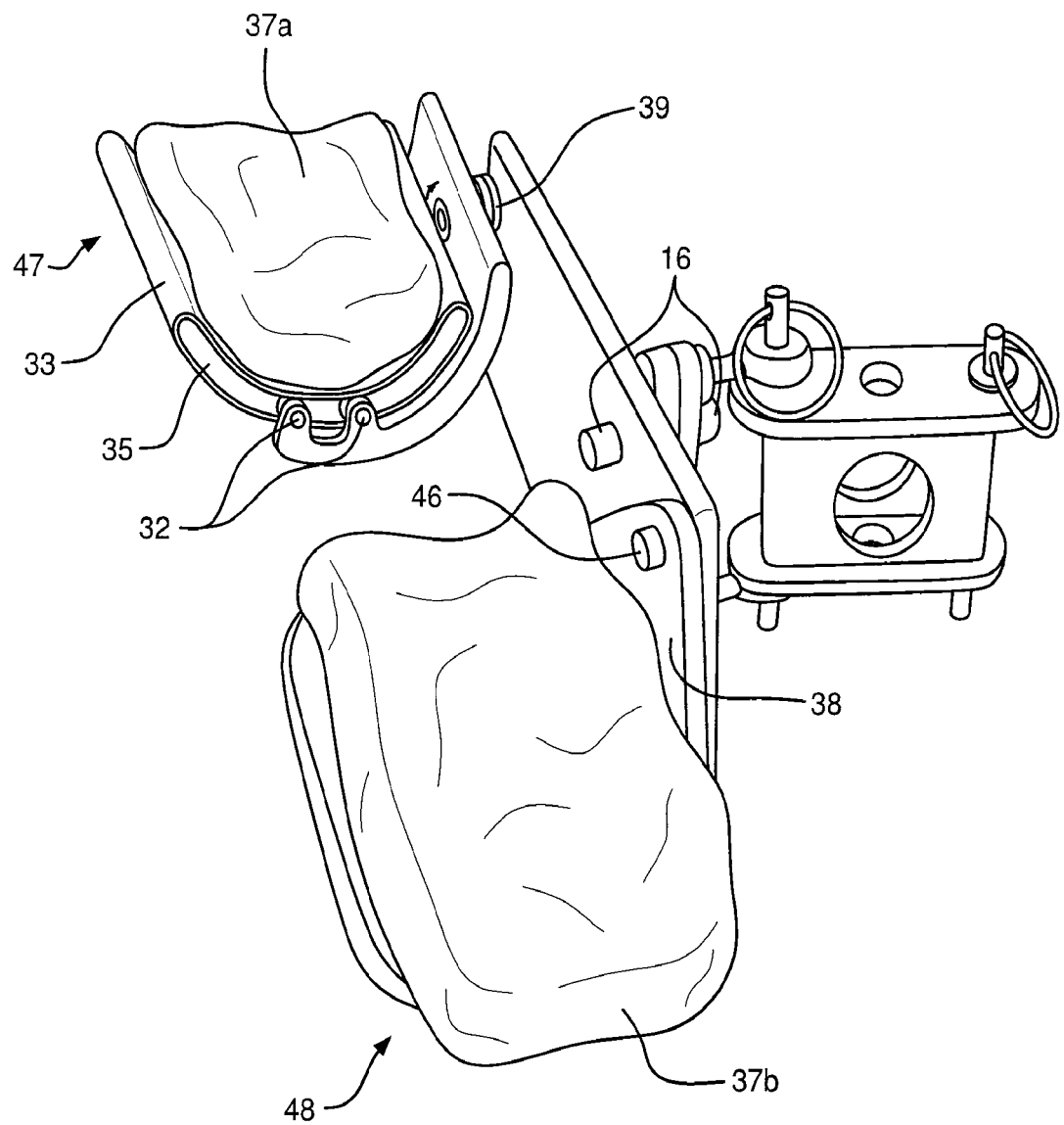
FIG. 13 shows an illustrative embodiment of a human arm support in which separately pivoting brackets support the heel-of-hand support structure and the forearm support structure and permit relative rotation between them.

FIG. 13 shows another version of the human arm support 10 in which parallel axles 39 and 46 respectively suspend the heel-of-hand and the forearm support assemblies 47 and 48, and permit relative counter-rotation between them, as well as mutual rotation around primary pivot axis 16. In this illustrative embodiment, the hand support assembly 47 also comprises roll plate 33, and track 35 and rollers 32 to permit relative axial rotation between hand-rest pad 37a and armrest pad 37b which is attached to or supported by curved support bracket 38

Figure 14:
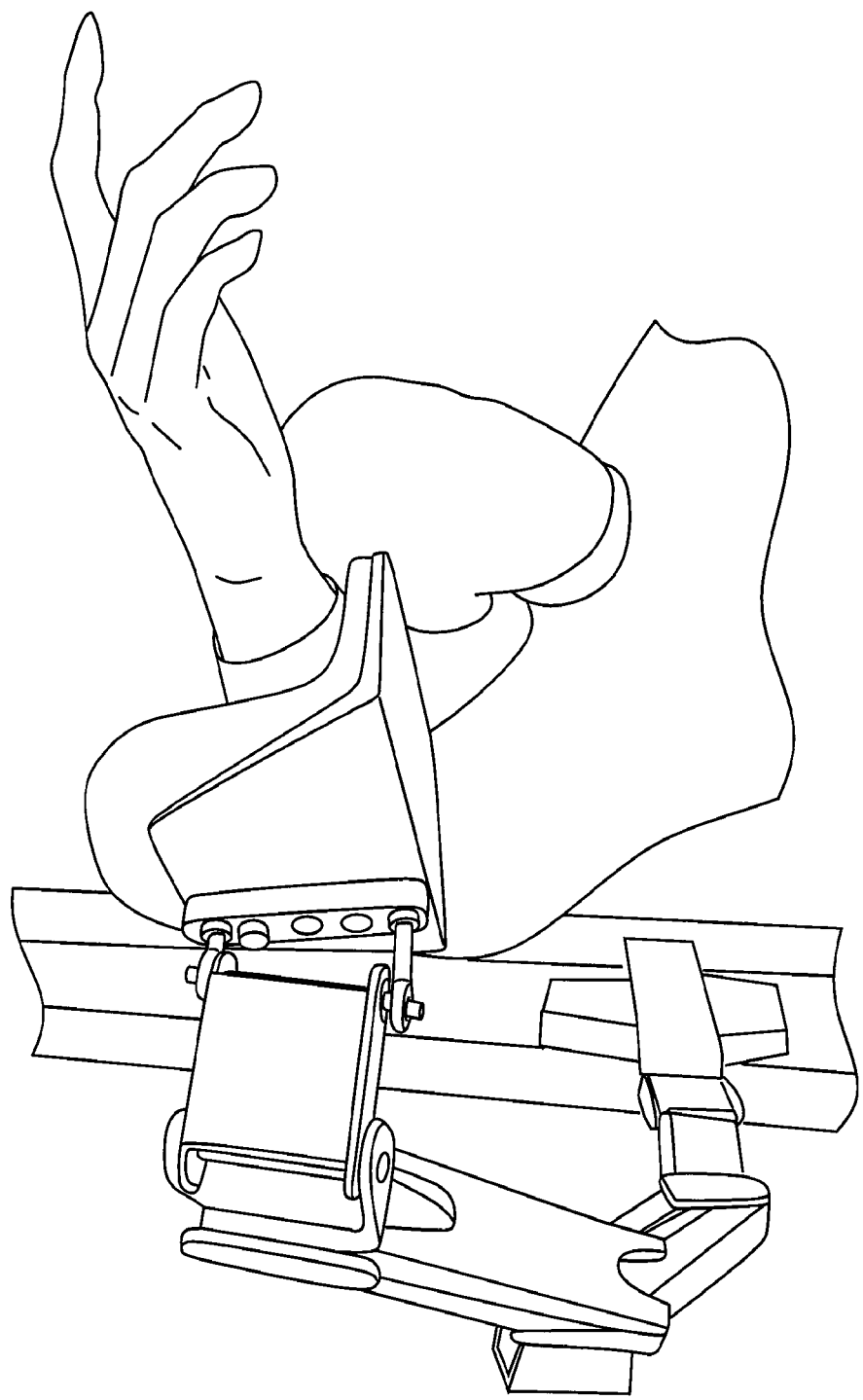
FIG. 14 shows a user's arm in a raised position while resting on a support structure according to an illustrative embodiment of the invention.

FIG. 14 shows a support arm apparatus in a raised position according to an illustrative embodiment of the invention, in which portions of mechanical arm 1 and human arm support 10 are above the user's shoulders.

Figure 15:
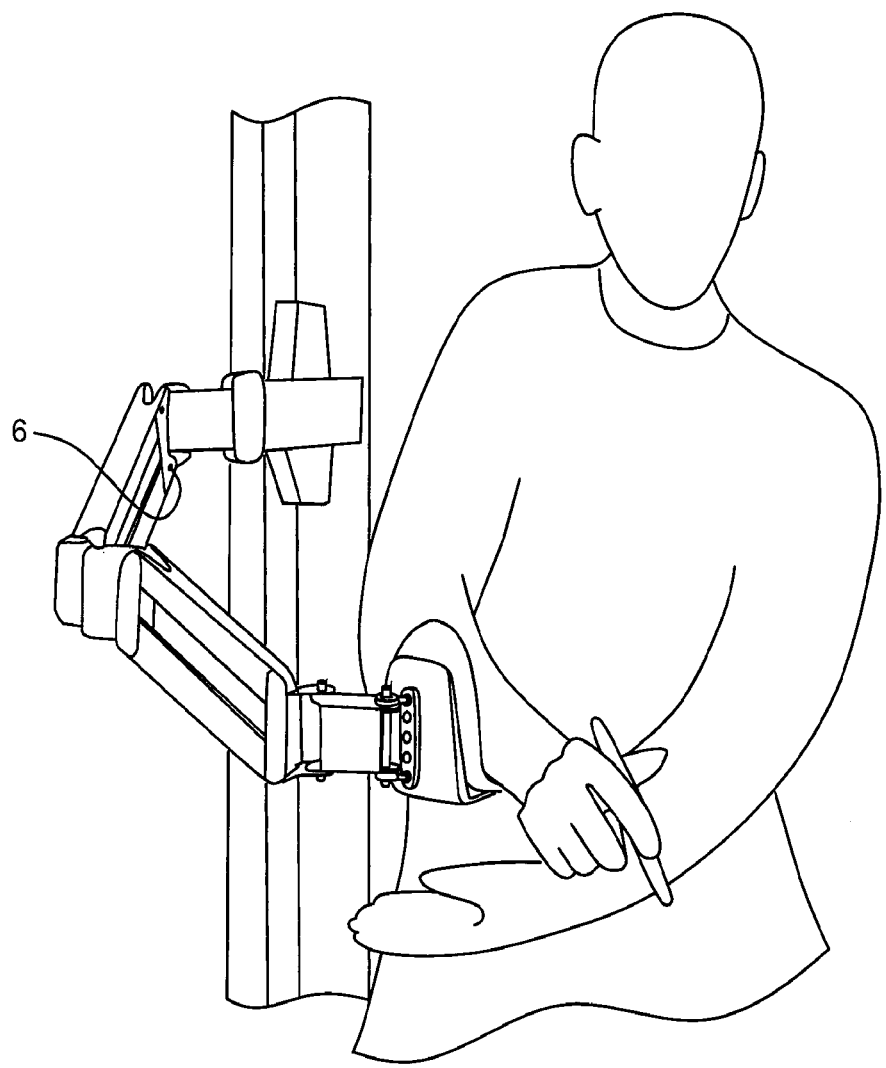
FIG. 15 depicts an arm support structure attached to a wall according to an illustrative embodiment of the invention.

FIG. 15 shows a support arm apparatus attached to a wall according to an illustrative embodiment of the invention. The apparatus is attached to the wall at the proximal arm segment 6 end. Various means of attachment can be used, provided they can withstand the stresses produced by the intended use of the apparatus and its weight. The support arm can be attached to other objects, such as tables or chairs. In an exemplary embodiment of the invention, the support arm structure is mounted to a harness worn by a user.

FIG. 16 depicts an illustrative embodiment of the invention, wherein the proximal end of the arm supporting mechanism 52 is mounted on a human-carried vest or harness 54 so that work can be performed in an ambulatory manner, with the arm (or arms) supported throughout. Various hybrid versions of this form of attachment are possible, permitting, for example, one or two arms to be attached at shoulder height to the rolling chair employed by a dentist or a surgeon, and thus keep the support apparatus always appropriately positioned for supporting the practitioner's forearm(s) for the entirety of extended work sessions.

Figure 17A:
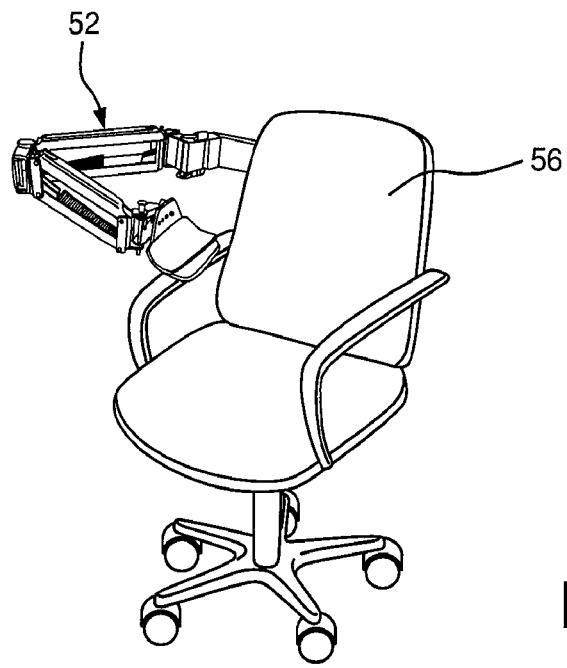
FIG. 17 depicts an arm supporting apparatus attached to a chair according to illustrative embodiments of the invention.
Figure 17B:
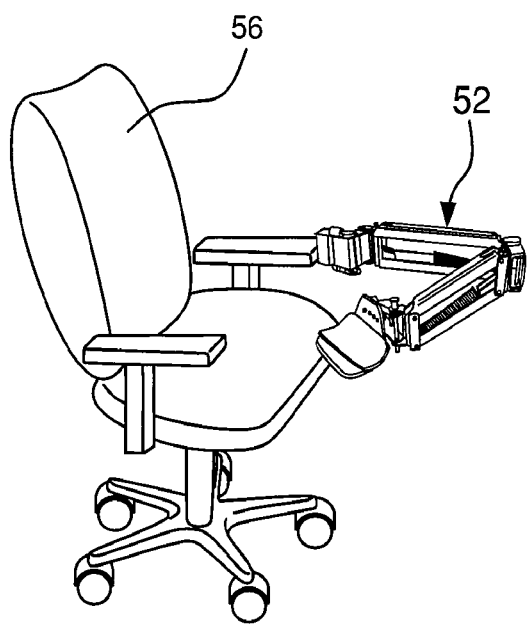
Figure 18:
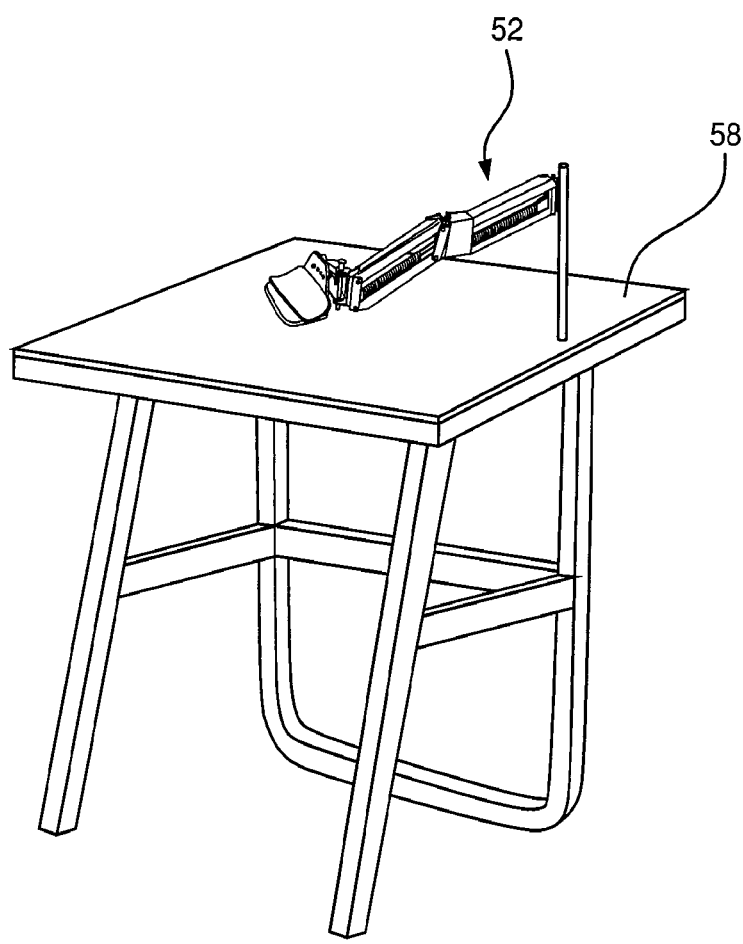
FIG. 18 depicts an apparatus attached to a table according to illustrative embodiments of the invention.

An arm supporting apparatus may be attached to various support structures, including, but not limited to tables and chairs. FIG. 17A depicts an arm supporting apparatus 52 attached to the back of a chair 56, FIG. 17B depicts an arm supporting apparatus 52 attached to the arm of a chair 56, and FIG. 18 depicts an apparatus 52 attached to a table 58, all according to illustrative embodiments of the invention.

Illustrative embodiments of the invention also provide for user-adjustment of lifting forces and pivot-axis offsets to tailor support performance for varying human arm weights, lengths, densities and operator preferences, and also to accommodate the bulk and weight of any required protection and/or isolation apparel. Equipoising arm supports can preferably be hand-adjusted to provide the desired lift.

In another illustrative embodiment of the invention, a centering mechanism, impelled by cams or a resilient mechanism for example, helps maintain lateral neutrality of position and counteract the tendency of pivoted inter-connected links to be laterally unstable due to accumulated component and bearing tolerances or other reasons.

Hinges, such as those described in patent application PCT/US2008/056511, incorporated herein by reference, also are suitable for use with illustrative embodiments of the invention. Application PCT/US2008/056511 describes a 'biased hinge' that may further improve arm performance by helping to maintain the selected lateral position of the arm segments (which is sometimes termed 'centering' but is not restricted to a bias to a symmetrically centered position).

Embodiments of the invention may also provide a 'docking/undocking' mechanism to permit the upward bias at the distal end of the arm mechanism to be restrained at a convenient position and height so that the human operator can un-dock it instantly by depressing the support surface and moving it laterally. Illustrative hardware includes a hook and mating eye, that permits immobilizing the entire support arm at a convenient position and height by, for example, simply swinging over to that position and permitting the hook to rise into the receiving eye. The operator can then lift off his or her own arm to perform other parts of the work that do not require arm support.

Illustrative embodiments of the invention may also be mounted to a harness worn by an ambulatory worker and allow the performance of protracted tasks with reduced or eliminated arm fatigue often associated with of self-support, without exerting undue influence on the arm and/or wrist throughout the operative extent of human reach and the area of work accessible by foot. Any harness that can support the weight of the apparatus, portion of the human body resting on the apparatus, and any devices attached thereto, and that allows for the required amount of movement, is suitable. Harnesses are preferably also ergonomically designed with comfort of the wearer in mind.

Note that other combinations and permutations permitting angular independence between heel of hand and forearm, including those separately disclosed by FIGS. 11, 12 and 13, and descriptions thereof, are contemplated within the scope of the invention.

Following is additional information for regarding the claim language and embodiments described herein.

Reference to "horizontal" and "vertical" throughout is made in a broad sense and is intended to include positions that are about horizontal or vertical. It is further noted that in certain embodiments of the invention, horizontal components can be substituted for vertical components and vice versa.

An upper body appendage is used herein to mean any portion of the appendage that includes the arm, hand and wrist. Throughout the application, the terms "arm" and "hand" include any portions thereof and in some instances can also include the wrist or portions thereof.

Components "attached" or "connected" to the articulating support arm can be attached or connected directly or indirectly, such as to an end block, bracket, etc.

The support to which the articulating support structure can be mounted can be mobile, such as a cart, dolly, or person, can be stationary, such as a post, beam, chair, or table.

Though the invention is described with reference to the particular embodiments herein set forth, it is understood that the present disclosure is made only by way of example and that numerous changes in the details of construction may be resorted to without departing from the spirit and scope of the invention. Accordingly, it is intended that the invention not be limited to the specific illustrative embodiments, but be interpreted within the full spirit and scope of the claims and their equivalents.

The invention claimed is:

1. An upper body appendage support apparatus comprising:
at least one articulated support structure having;
a plurality of segments pivotally connected in series by pan pivots;
wherein at least one of the segments of the plurality of segments is a parallelogram segment having a resilient mechanism that provides a dynamic lifting force that biases the at least one of the segments of the plurality of arm segments upwardly in a lifting plane;
an upper body appendage support structure pivotably attached to the articulating support structure;
the upper body appendage support structure comprising;
an upper body appendage rest, the rest having a first section configured to support a forearm and a second section configured to support an appendage portion below the forearm;
the first and second sections of the upper body appendage rest, each comprising a curved surface of sufficient size and shape to support a user's forearm and an appendage portion below the forearm, respectively, without the user grasping either section of the rest with the user's hand, thereby leaving the hand free to grasp an object, wherein the surfaces are free from obstructions that would prohibit use of the hand to grasp an object;
one or both of the first and second sections having;
a roll mechanism connected to the upper body appendage rest for rotation about an axis substantially parallel to a user's arm to allow rotation of upper body appendages without lifting from, or sliding on upper body appendage support structure resting surface; and
a roll mechanism functionally connected to the first section and a roll mechanism functionally connected to the second section, wherein the axes of rotation of the roll mechanisms are in line with one another.

2. An upper body appendage support apparatus comprising at least one articulated support structure having at least one parallelogram segment having a resilient mechanism that provides a dynamic lifting force that biases the segment upwardly in a lifting plane;
an upper body appendage support structure pivotally attached to the articulating support structure;
the upper body appendage support structure comprising;
a first section having a first upper body appendage rest, the rest having a surface on which a first portion of an upper body appendage can rest; and
a second section having a second upper body appendage rest, the rest having a surface on which a second portion of an upper body appendage can rest;
wherein the first or second sections of the upper body appendage rest each comprises a curved surface of sufficient size and shape to support a user's first portion of an upper body appendage and a user's second portion of an upper body appendage, respectively, without the user grasping the rest with the user's hand, thereby leaving the hand free to grasp an object, wherein the surfaces are free from obstructions that would prohibit use of the hand to grasp an object;
wherein the upper body appendage support structure is pivotally connected to the articulated support structure at a first pivot to provide rotation of the upper body appendage support structure about an axis to provide tilt motion of the upper body appendage support structure; and one or more roll mechanisms connected to the upper body appendage rest for rotation about an axis substantially parallel to a user's arm to allow rotation of upper body appendages without lifting from, or sliding on upper body appendage support structure resting surface;

wherein the upper body appendage support structure is further pivotally connected to the articulating support structure at a second pivot to provide rotation of the upper body appendage support structure about an axis to provide pan motion of the upper body appendage support structure.

3. An upper body appendage support apparatus comprising at least one articulated support structure;

an upper body appendage support structure movably attached to the articulating support structure;

the upper body appendage support structure comprising;

a first section configured to accommodate a first arm portion;

a second section configured to accommodate a second arm portion below the first arm portion;

one or more roll mechanisms to allow rotation of upper body appendages without lifting from, or sliding on upper body appendage support structure resting surface;

wherein at least one of the roll mechanisms comprises:

a roll track having a curved track;

one or more track rollers configured to roll on the track to impart rotational capabilities to the resting surface; and a surface on which at least a portion of an upper body appendage can rest;

wherein the upper body appendage support structure is pivotally connected to the articulated support structure at a first pivot to provide rotation of the upper body appendage support structure about an axis to provide tilt motion of the upper body appendage support structure;

wherein the upper body appendage support structure is further pivotally connected to the articulating support structure at a second pivot to provide rotation of the upper body appendage support structure about an axis to provide pan motion of the upper body appendage support structure; and wherein the articulated support structure counteracts the weight of the upper body appendage support structure and any weight thereon by providing a lifting force.

4. An upper body appendage support apparatus comprising at least one articulated support structure having:

a plurality of segments pivotally connected in series by pan pivots;

wherein at least one of the segments of the plurality of segments is a parallelogram segment having a resilient mechanism that provides a dynamic lifting force that biases the at least one of the segments of the plurality of segments upwardly in a lifting plane;

an upper body appendage support structure movably attached to the articulating support structure;

the upper body appendage support structure comprising;

an upper body appendage rest, the rest comprising a curved surface of sufficient size and shape to support a user's forearm without the user grasping the rest with the user's hand, thereby leaving the hand free to grasp an object, wherein the surface is free from obstructions that would prohibit use of the hand to grasp an object;

the upper body appendage support structure pivotally connected to the articulated support structure by a single tilt pivot positioned to one side of the upper body appendage support structure;

the upper body appendage support structure further pivotally connected to the articulating support structure at a pan pivot, wherein the pan pivot is positioned to the one side of the upper body appendage support structure on which the tilt pivot is positioned.

5. The upper body appendage support apparatus of claim 4 wherein axes of rotation of the pan pivot and tilt pivot intersect.

6. The upper body appendage support apparatus of claim 4 wherein the upper body appendage rest surface is concave.

7. The upper body appendage support apparatus of claim 4 wherein the upper body appendage rest surface is semi-cylindrical.

8. An upper body appendage support apparatus comprising:

an articulated support structure comprising:
    a first segment;
    a second segment;
    a third segment;
    the first segment, second segment and third segment pivotally connected in series;
    the first segment connected to the second segment by a first pan pivot;
    the second segment further connected to the third segment by a second pan pivot;
    at least one of the first, second and third segments being a parallelogram segment having a resilient mechanism that provides a dynamic lifting force that biases the segment upwardly in a lifting plane;

an upper body appendage support structure having an upper body appendage rest, the rest comprising a curved, surface of sufficient size and shape to support a user's forearm without the user grasping the rest with the user's hand, thereby leaving the hand free to grasp an object, wherein the surface is free from obstructions that would prohibit use of the hand to grasp an object;

a tilt pivot connecting the upper body appendage support structure to the first segment at an end of the first segment opposing the first pan pivot, the tilt pivot disposed at a level at, or above the curved, rest surface;

a third pan pivot connecting the upper body appendage support structure to the first segment at an end of the first segment opposing the first pan pivot, the third pan pivot disposed adjacent to the upper body appendage rest; and wherein rotation about the first pan pivot, second pan pivot and third pan pivot is in a plane substantially perpendicular to the lifting plane.

9. The support apparatus of claim 8 comprising a mounting component attached to the articulating support structure at an end opposing the upper body appendage rest for mounting the apparatus to a support.

10. The support apparatus of claim 9 wherein the apparatus is mounted to a harness that can be worn by a user.

11. The support apparatus of claim 8 comprising at least one biased hinge attached to at least one of the first, second or third segments and further attached to one of the other first, second or third segments or a support for biasing the articulating support structure in a plane substantially perpendicular to a lifting plane of the articulating support structure.

12. A chair comprising a support structure according to claim 8 operatively connected thereto.

13. A table comprising a support structure according to claim 8 operatively connected thereto.

14. A method of performing a task comprising:
providing a support structure according to claim 8;
placing an upper body appendage on the resting surface having the hand thereof free to perform a task.

15. An upper body appendage support apparatus comprising:
an articulating support structure comprising:
at least two segments connected in series;
the at least two segments including a first segment and a second segment, the first segment connected to the second segment by a first pan pivot;
at least one segment of the at least two segments having a resilient mechanism providing a dynamic lifting force to bias the at least one segment of the at least two segments upwardly in a lifting plane;
an upper body appendage support structure having an upper body appendage rest, the rest having a surface on which at least a portion of an upper body appendage can rest;
the upper body appendage support structure pivotally connected to the first segment of the articulated support structure by a tilt pivot at a tilt pivot point on the upper body appendage support structure;
a plurality of tilt pivot connection locations to selectively connect the location of the tilt pivot with respect to the upper body appendage support structure;
a roll mechanism attached to the upper body appendage rest;
the roll mechanism comprising:
a track engaged with complimentary roll mechanism components and having a roll motion axis substantially parallel to the user's forearm; and
a mounting component attached to the articulating support structure at an end opposing the upper body appendage support structure.

16. The support structure of claim 15 wherein: the upper body support structure comprises a first section configured to accommodate a first arm portion and a second separate section configured to accommodate a second arm portion below the first arm portion wherein the first and second arm portions are jointed to one another.

17. An upper body appendage support apparatus comprising:
an articulated support structure comprising:
a first segment;
a second segment;
a third segment;
the first segment, second segment and third segment pivotally connected in series;
the first segment connected to the second segment by a first pan pivot;
the second segment further connected to the third segment by a second pan pivot;
at least one of the first, second and third segments being a parallelogram segment having a resilient mechanism that provides a dynamic lifting force that biases the segment upwardly in a lifting plane;
at least one of the first, second and third segments having a resilient mechanism that provides a dynamic lifting force that biases the segment upwardly in a lifting plane;
an upper body appendage support structure having an upper body appendage rest, the rest having a surface on which at least a portion of an upper body appendage can rest;
a tilt pivot connecting the upper body appendage support structure to the first segment at an end of the first segment opposing the first pan pivot;
a third pan pivot connecting the upper body appendage support structure to the first segment at an end of the first segment opposing the first pan pivot, the third pan pivot disposed adjacent to the upper body appendage rest; and
wherein rotation about the first pan pivot, second pan pivot and third pan pivot is in a plane substantially perpendicular to the lifting plane; and
a docking mechanism comprising a first docking component attached to the articulated support structure, the first docking component engageable with a stationary second docking component to restrain an upward bias of the first segment of the articulating support structure.

18. An upper body appendage support apparatus comprising:
an articulated support structure comprising:
a first segment;
a second segment;
a third segment;
the first segment, second segment and third segment pivotally connected in series;
the first segment connected to the second segment by a first pan pivot;
the second segment further connected to the third segment by a second pan pivot;
at least one of the first, second and third segments having a resilient mechanism that provides a dynamic lifting force that biases the segment upwardly in a lifting plane;
an upper body appendage support structure having an upper body appendage rest, the rest having a surface on which at least a portion of an upper body appendage can rest;
a tilt pivot connecting the upper body appendage support structure to the first segment at an end of the first segment opposing the first pan pivot;
a third pan pivot connecting the upper body appendage support structure to the first segment at an end of the first segment opposing the first pan pivot, the third pan pivot disposed adjacent to the upper body appendage rest; and
wherein rotation about the first pan pivot, second pan pivot and third pan pivot is in a plane substantially perpendicular to the lifting plane; and
a plurality of tilt pivot connection locations to selectively connect the location of the tilt pivot with respect to the upper body appendage support structure.

19. The support apparatus of claim 18 wherein the tilt pivot connection location can be adjusted substantially vertically.

20. The support apparatus of claim 18 wherein the tilt pivot connection location can be adjusted substantially horizontally.

21. An upper body appendage support apparatus comprising:
an articulated support structure comprising:
a first segment;
a second segment;
a third segment;
the first segment, second segment and third segment pivotally connected in series;
the first segment connected to the second segment by a first pan pivot;
the second segment further connected to the third segment by a second pan pivot;
at least one of the first, second and third segments having a resilient mechanism that provides a dynamic lifting force that biases the segment upwardly in a lifting plane;

an upper body appendage support structure having an upper body appendage rest, the rest having a surface on which at least a portion of an upper body appendage can rest;

a tilt pivot connecting the upper body appendage support structure to the first segment at an end of the first segment opposing the first pan pivot;

a third pan pivot connecting the upper body appendage support structure to the first segment at an end of the first segment opposing the first pan pivot, the third pan pivot disposed adjacent to the upper body appendage rest; and wherein rotation about the first pan pivot, second pan pivot and third pan pivot is in a plane substantially perpendicular to the lifting plane;

wherein the upper body appendage rest and the associated surface comprises a first section on which a first arm portion can rest and a second separate section, pivotably attached to the first section, on which a second arm portion below the first arm portion can rest wherein the first and second arm portions are jointed to one another;

one or more roll mechanisms connected to the upper body appendage rest for rotation about an axis substantially in line with a user's arm to allow rotation of upper body appendages without lifting from, or sliding on upper body appendage support structure resting surface; and wherein at least one of the roll mechanisms comprises:

a roll track having a curved track; and one or more track rollers configured to roll on the track to impart rotational capabilities to the resting surface.

22. An upper body appendage support apparatus comprising at least one articulated support structure having:

a plurality of segments pivotally connected in series by pan pivots;

wherein at least one of the segments of the plurality of segments is a parallelogram segment having a resilient mechanism that provides a dynamic lifting force that biases the at least one of the segments of the plurality of segments upwardly in a lifting plane;

an upper body appendage support structure movably attached to the articulating support structure;

the upper body appendage support structure comprising;

an upper body appendage rest, the rest having a surface on which at least a portion of an upper body appendage can rest;

wherein the upper body appendage support structure is pivotally connected to the articulated support structure at a tilt pivot;

wherein the upper body appendage support structure is further pivotally connected to the articulating support structure at a pan pivot, wherein the pan pivot is displaced to the side of the upper body appendage support structure; and a docking mechanism comprising a first docking component attached to the articulated support structure, the first docking component engageable with a stationary second docking component to restrain an upward bias of the first segment of the articulated support structure.

23. An upper body appendage support apparatus comprising at least one articulated support structure having:

a plurality of segments pivotally connected in series by pan pivots;

wherein at least one of the segments of the plurality of segments is a parallelogram segment having a resilient mechanism that provides a dynamic lifting force that biases the at least one of the segments of the plurality of segments upwardly in a lifting plane;

an upper body appendage support structure movably attached to the articulating support structure;

the upper body appendage support structure comprising;

an upper body appendage rest, the rest having a surface on which at least a portion of an upper body appendage can rest;

wherein the upper body appendage support structure is pivotally connected to the articulated support structure at a tilt pivot;

wherein the upper body appendage support structure is further pivotally connected to the articulating support structure at a pan pivot, wherein the pan pivot is displaced to the side of the upper body appendage support structure; and a plurality of tilt pivot connection locations to selectively connect the location of the tilt pivot with respect to the upper body appendage support structure.

24. An upper body appendage support apparatus comprising:

an articulated support structure comprising:

a first segment;

a second segment;

a third segment;

the first segment, second segment and third segment pivotally connected in series;

the first segment connected to the second segment by a first pan pivot;

the second segment further connected to the third segment by a second pan pivot;

at least one of the first, second and third segments being a parallelogram segment having a resilient mechanism that provides a dynamic lifting force that biases the segment upwardly in a lifting plane;

an upper body appendage support structure having an upper body appendage rest, the rest having a surface on which at least a portion of an upper body appendage can rest;

a tilt pivot connecting the upper body appendage support structure to the first segment at an end of the first segment opposing the first pan pivot;

a third pan pivot connecting the upper body appendage support structure to the first segment at an end of the first segment opposing the first pan pivot, the third pan pivot disposed adjacent to the upper body appendage rest; and wherein rotation about the first pan pivot, second pan pivot and third pan pivot is in a plane substantially perpendicular to the lifting plane; and the upper body appendage rest and the associated surface comprises a first section on which a first arm portion can rest and a second separate section, pivotably attached to the first section on which a second arm portion below the first arm portion can rest wherein the first and second arm portions are jointed to one another.

25. The support apparatus of claim 24 wherein the second section of the upper body appendage support is pivotally attached to the articulated support structure.

26. The support apparatus of claim 24, further comprising one or more roll mechanisms connected to the upper body appendage rest for rotation about an axis substantially in line with a user's arm to allow rotation of upper body appendages without lifting from, or sliding on upper body appendage support structure resting surface.

27. The support apparatus of claim 26 comprising a roll mechanism functionally connected to the first section and a roll mechanism functionally connected to the second section, wherein the axes of rotation of the roll mechanisms are in line with one another.

28. The support apparatus of claim 26 wherein the roll mechanism provides a degree of rotation of the resting surface is in the range of about 20° to about 30°.

29. An upper body appendage support apparatus comprising
- at least one articulated support structure having:
- a plurality of segments pivotally connected in series by pan pivots;
- wherein at least one of the segments of the plurality of segments is a parallelogram segment having a resilient mechanism that provides a dynamic lifting force that biases the at least one of the segments of the plurality of segments upwardly in a lifting plane;
- an upper body appendage support structure movably attached to the articulating support structure;
- the upper body appendage support structure comprising;
- an upper body appendage rest, the rest having a surface on which at least a portion of an upper body appendage can rest;
- wherein the upper body appendage support structure is pivotally connected to the articulated support structure at a tilt pivot;
- wherein the upper body appendage support structure is further pivotally connected to the articulating support structure at a pan pivot, wherein the pan pivot is displaced to the side of the upper body appendage support structure; and
- wherein at least one of the roll mechanisms comprises:
- a roll track having a curved track;
- one or more track rollers configured to roll on the track to impart rotational capabilities to the resting surface.

* * * * *